(12) United States Patent
Browning et al.

(10) Patent No.: US 7,030,080 B2
(45) Date of Patent: Apr. 18, 2006

(54) LYMPHOTOXIN-β, LYMPHOTOXIN-β COMPLEXES, PHARMACEUTICAL PREPARATIONS AND THERAPEUTIC USES THEREOF

(75) Inventors: Jeffrey Browning, Brookline, MA (US); Carl F. Ware, Riverside, CA (US)

(73) Assignees: Biogen, Inc., Cambridge, MA (US); University of California, Oakland, CA (US)

( * ) Notice: Subject to any disclaimer, the term of this patent is extended or adjusted under 35 U.S.C. 154(b) by 0 days.

(21) Appl. No.: 10/040,281

(22) Filed: Nov. 7, 2001

(65) Prior Publication Data

US 2003/0143210 A1 Jul. 31, 2003

Related U.S. Application Data

(63) Continuation of application No. 08/466,254, filed on Jun. 6, 1995, now abandoned, which is a division of application No. 08/222,614, filed on Apr. 1, 1994, now abandoned, which is a continuation of application No. 07/990,304, filed on Dec. 4, 1992, now abandoned, which is a continuation-in-part of application No. PCT/US91/04588, filed on Jun. 27, 1991, now abandoned, and a continuation-in-part of application No. 07/544,862, filed on Jun. 27, 1990, now abandoned.

(51) Int. Cl.
*A61K 38/00* (2006.01)

(52) U.S. Cl. .................... 514/2; 424/143.1; 424/134.1; 514/8

(58) Field of Classification Search .............. 424/134.1, 424/143.1; 514/2, 8
See application file for complete search history.

(56) References Cited

U.S. PATENT DOCUMENTS

| 4,338,397 A | 7/1982 | Gilbert et al. |
| 4,758,549 A | 7/1988 | Mitsuhashi et al. |
| 4,822,605 A | 4/1989 | Powell |
| 4,849,509 A | 7/1989 | Thurin et al. |

FOREIGN PATENT DOCUMENTS

| EP | 0367575 | 5/1990 |

OTHER PUBLICATIONS

Browning et al., J. Exp. Med. vol. 183:867–878, 1996.*
Mackay et al., J. Immunology vol. 159:3299–3310, 1997.*
Browning et al., The Journal of Immunology. vol. 147(4):1230–1237, Aug. 15, 1991.*
Abe, Y., et al. "Expression of membrane–associated lymphotoxin/tumor necrosis factor–beta on human lymphokine–activated killer cells." Jpn J Cancer Res. 1991 Jan; 82(1):23–6.

Abe, Y., et al., "Studies of membrane–associated and soluble (secreted) lymphotoxin in human lymphokine–activated T–killer cells in vitro." *Lymphokine Cytokine Res*. 1992 Apr; 11(2): 115–21.

Abersold, et al., "Internal amino acid sequence analysis of proteins separated by one–or two–dimensional gel electrophoresis after in situ protease digestion on nitrocellulose." PNAS. 1987; 84:6970–4.

Aggarwal, B.B., et al., "Primary structure of human lymphotoxin derived from 1788 lymphoblastoid cell line." *J. Biol Chem*. 1985 Feb. 25; 260(4):2334–44.

Akashi, M., et al. "Lymphotoxin: stimulation and regulation of colony–stimulating factors in fibroblast." *Blood*. 1989 Nov. 15; 74(7)2383–90.

Anderson, W.F. "Human gene therapy." *Science*. 1992 May 8; 256(5058):808–13.

Anderson, U., et al. "Characterization of individual tumor necrosis factor alpha–and beta–producing cells after polyclonal T cell activation." *J. of Immun. Meth.* 1989; 123:233–40.

Andrews, J.S., et al. "Characterization of the receptor for tumor necrosis factor (TNF) and lymphotoxin (LT) on human T lymphocytes." *J Immunol*. 1990 Apr. 1; 144(7):2582–91.

Androlewicz, M.J., et al. "Lymphotoxin is expressed as a heteromeric complex with a distinct 33–kDa glycoprotein on the surface of an activated human T cell hybridoma." *J Biol Chem.* 1992 Feb. 5; 267(4):2542–7.

Armitage, R.J., et al. "Molecular and biological characterization of a murine ligan for CD40." *Nature*. 1992 May 7; 357(6373):80–2.

Badenhoop, K., et al. "TNF–alpha gene polymorphisms in type 1 (insulin–dependent) diabetes mellitus." *Diabetologia*. 1989 Jul; 32(7):445–8.

(Continued)

*Primary Examiner*—Sean McGarry
(74) *Attorney, Agent, or Firm*—Lahive & Cockfield; Amy Mandragouras

(57) ABSTRACT

This invention relates to lymphotoxin-β, a lymphocyte membrane type protein. This protein is found on the surface of a number of cells, including phorbol ester (PMA) stimulated T cell hybridoma II-23.D7 cells. This invention also relates to complexes formed between lymphotoxin-β and other peptides such as lymphotoxin-α and to complexes comprising multiple subunits of lymphotoxin-β. These proteins and complexes are useful in holding LT-α formed within the cell on the cell surface where the LT-α/LT-β complex may act as an inflammation regulating agent, a tumor growth inhibiting agent, a T cell inhibiting agent, a T cell activating agent, an autoimmune disease regulating agent, or an HIV inhibiting agent. Furthermore, the antitumor activity of the LT-α/LT-β complex may be delivered to tumor cells by tumor infiltrating lymphocytes (TILs) transfected with the gene for LT-β.

5 Claims, 18 Drawing Sheets

OTHER PUBLICATIONS

Beutler, B., et al. "The history, properties, and biological effects of cachectin." *Biochemistry*. 1988 Oct. 4; 27(20):7575–82.

Bringman, T.S., et al. "Monoclonal antibodies to human tumor necrosis factors alpha and beta: application for affinity purification, immunoassays, and a s structural probes." *Hybridoma*. 1987 Oct; 6(5):489–507.

Browning, J.L., et al. "Studies on the differing effects of tumor necrosis factor and lymphotoxin on the growth of several human tumor lines." *J. Immunol*. 1989 Sep. 15; 143(6):1859–67.

Browning, J.L, et al. "Lymphotoxin and an associated 33–kDa glycoprotein are expressed on the surface of an activated human T cell hybridoma," *J Immunol*. 1991 Aug. 15; 147(4):1230–7.

Cavender, D.E., et al. "Endothelial cell activation induced by tumor necrosis factor and lymphotoxin." *Am. J Pathol*. 1989 Mar; 134(3):551–60.

Cotran, R.S., et al. "Endothelial activation, its role in inflammatory and immune reactions." *Endothelial Cell Biology*. 1988; 335–47.

Damle, N.K., et al. "District regulatory effects of IL–4 and TNF–alpha during CD3–dependent and CD3–independent initiation of human T–cell activation." *Lymphokine Res*. 1989; 8(2):85–97.

Eck, M.J. et al., "The structure of tumor necrosis factor–alpha at 2.6 A resolution. Implications for receptor binding." *J. Biol. Chem*. 1989 Oct. 15; 264(29):17595–605.

Eck, M.J. et al. "The structure of human lynmphotoxin (tumor necrosis factor–beta) at 1.9–A resolution." *J. Biol Chem*. 1992 Feb. 5; 267(4):2119–22.

Farrah, T., et al. "Emerging cytokine family." *Nature*. 1992 Jul. 2; 358(6381):26.

Fuh, G., et al., "Rational design of potent antagonists to the human growth hormone receptor." *Science*. 1992 Jun. 19: 256(5064):1677–80.

Goeddel, D.V., et al. "Tumor necrosis factors: gene structure and biological activities." *Cold Spring Harb Symp Quant Biol*. 1986; 51:597–609.

Granger, G.A., et al. "Lymphocyte in vitro cytotoxicity: mechanisms of immune and non–immune small lymphocyte mediated target L cell destruction." *J Immunol*. 1968 Jul; 101(1):111–20.

Gray, P.W. "Molecular characterization of human lymphotoxin." *Lumphokines*. 1987; 13:199–208.

Gray, P.W., et al. "Cloning and expression of cDNA for human lymphotoxin, a lymphokine with tumour necrosis activity." *Nature*. 1984 Dec. 20–1985 Jan. 2; 312(5996):721–4.

Green, L.M. et al. "Cytotoxic lymphokines produced by cloned human cytotoxic T lymphocytes. I. Cytotoxins produced by antigen–specific and natural killer–like CTL are dissimilar to classical lymphotoxins." *J Immunol*. 1985 Dec; 135(6):4034–43.

Green, L.M., et al. "Rapid colorimetric assay for cell viability: application to the quantitation of cytotoxic and growth inhibitory lymphokines." *J Immunol Methods*. 1984 May 25; 70(2):257–68.

Hiserodt, J.C. et al. "Identification of membrane–associated lymphotoxin (LT) on mitogen–activated human lymphocytes using heterologous anti–LT antisera in vitro." *Cell Immunol*. 1977 Dec; 34(2):326–39.

Itoh, N., et al., "The polypeptide encoded by the cDNA for human cell surface antigen Fas can mediate apoptosis." *Cell*. 1991 Jul. 26; 66(2):233–43.

Jones, E.Y., et al. "Structure of tumnour necrosis factor." *Nature*. 1989 Mar. 16; 338(6212):225–8.

Kasid, A., et al. "Human gene transfer: characterization of human tumor–infiltrating lymphocytes as vehicles for retroviral–mediated gene transfer in man." *Proc Natl Sci USA*. 1990 Jan; 87(1):473–7.

Kinkhabwala, M., et al. "A novel addition to the T cell repertory. Cell surface expression of tumor necrosis factor/cachetin by activate normal human T cells." *J Exp Med*. 1990 Mar. 1; 171(3):941–6.

Krieglr, M., et al. "A novel form of TNF/cachectin is a cell surface cytotoxic transmembrane protein: ramifications for the complex physiology of TNF." *Cell*. 1988 Apr. 8; 53(1):45–53.

Liang, C.M., et al. "Production and characterization of monoclonal antibodies against recombinant human tumor necrosis factor/cachectin." *Biochem Biophys Res Commun*. 1986 Jun. 13; 137(2):847–54.

Liu, C.C., et al. "Identification, isolation, and characterization of a novel cytotoxin in murine cytolytic lymphocytes." *Cell*. 1987 Nov. 6; 51(3):393–403.

Liu, C.C. et al. "Identification and characterization of a membrane–bound cytotoxin of murine cytolytic lymphocytes that is related to tumor necrosis factor/cachectin." *Proc Natl Acad Sci USA*. 1989 May: 86(9):3286–90.

Luetig, B., et al. "Evidence for the existence of two forms of membrane tumor necrosis factor: an integral protein and a molecule attached to its receptor." *J Immunol*. 1989 Dec. 15; 143(12):4034–8.

Mallet, S., et al. "A new superfamily of cell suface proteins related to the nerve growth factor receptor." *Immunol Today*. 1991 Jul.; 12(7):220–3.

Old, L.J. "Tumor necrosis factor (TNF)." *Science*. 1985 Nov. 8; 230(4726):630–2.

Paul, N.L., et al. "Lymphotoxin." *Annu. Rev Immunol*. 1988; 6:407–38.

Paul, N.L., et al. "Lymphotoxin activation by human T–cell leukemia virus type I–infected cell lines: role for NF–kappa B." *J Virol*. 1990 Nov.; 64(11):5412–9.

Pennica, D., et al. "Human tumour necrosis factor: precursor structure, expression and homology to lynmphotoxin." *Nature*. 1984 Dec. 20–1985 Jan. 2; 312(5996):724–9.

Peterson, A., et al. "Monoclonal antibody and ligand binding sites of the T cell erythrocyte receptor (CD2)." *Nature*. 1987 Oct. 29–Nov. 4; 329(6142):842–6.

Pociot, F., et al. "A tumour necrosis factor beta gene polymorphism in relation to monokine secretion and insulin–dependent diabetes mellitus." *Scand J Immunol*. 1991 Jan.; 33(1):37–49.

Ranges, G.E., et al. "Tumor necrosis factor–alpha as a proliferative signal for an IL–2–dependent T cell line: strict species specificity of action." *J Immunol*. 1989 Feb. 15; 142(4):1203–8.

Ranges, G.E., et al. "Tumor necrosis factor alpha/cachectin is a growth factor for thymocytes. Synergisitc interactions with other cytokines."*J Exp Med*. 1988 Apr. 1; 167(4):1472–8.

Roodman, G.D., et al. "Tumor necrosis factor–alpha and hematopoietic progenitors: effects of tumor necrosis factor on the growth of erythroid progenitors CFU–E and BFU–E and the hematopoietic cell lines K562, HL60, and HEL cells." *Exp Hematol*. 1987 Oct; 15(9):928–35.

\* cited by examiner

N-terminus:

G L E G R G x R L Q G R G S L L L A V A G A T G L V T L L - - V P I

Tryptic Peptides

```
                         10              20              30              40              50              60
                         -               -               -               -               -               -
hTNF      MSTESMIRD hTNF      VELAEEALPKKTGGPQGSRRCLFLSLFSFLIVAGATTLFCLLHFGVIGPQ
mCD40L    MIETYSQPSPRSVATGLPASMKIFMYLLTVFLITQMIGSVLFAVYLHRR
hP33      GLEGRGGRLQGRGSLLAVAGATSLVTLLAVPITVLAVLALVPQDQ
hLT               MTPPERLFLPRVCGTTLHLLLGLLLVLLPGAQGLPGVGLT hTNF      ----REE--FPRD----------------------------------
mCD40L    LDKVEEEVNLHEDFVFIKKLKRCNKGEGSLSLLNCEEMRRQFEDLVKDIT
hP33      GGLVTETADPGAQAQ---------------------------------
hLT       ------------------------------------------------
```

FIG. 14A

| FIG. 14A |
|----------|
| FIG. 14B |

FIG. 14

```
hTNF     LSLISPLPQAVRSSSRTPSDKPVAHVVANPQAEGQ--LQWLNRRANALLA
mCD40L   LNKEEKKENSFEMQRGDEDPQIAAHVVSEANSNAASVLQWAKKGYYTMKS
hP33     QGLGFQKLPEEEPETDLSPGLPAAHLIGAPLK-GQ-GLQWETTKEQAFLT
hLT      PSAAQTARQHPKMHLAHSTLKPAAHLIGDPSK--QNSLLWRANTDRAFLQ hTNF     NGVELRD-NQLVVPSEGLYLIYSQVLFKGQGCPSTHVLLTHTISRIAVSY
mCD40L   NLVMLENGKQLTVKREGLYYVYTQVTFCSNREPSSQRPFIVGLWLKPSIG
hP33     SGTQFSDAEGLALPQDGLYYLYCLVGYRGRAPPGGGDPQGRSVTLRSSLY
hLT      DGFSLSNNS--LLVPTSGIYFVYSQVVFSGKAYSPKATSSPLYLAHEVQLF hTNF     QTKVN-------LLSAIKSPCQRETPEGAEAK--P-WYEPIYLGGVFQLE
mCD40L   SER---------ILLKAANTHSSSQLCEQQ-------SVHLGGVFELQ
hP33     RAGGAYGPGTPELLLEGAETVTPVLDPARRQGYGPLWYTSVGFGGLVQLR
hLT      SS--QYPFHVP-LLSSQK-MVYPGLQE---------P-WLHSMYHGAAFQLT hTNF     KGDRLSAEINRPDY-LDFAESGQVYFGIIAL
mCD40L   AGASVFVNVT--EASQVIHRVGFSSFGLLKL
hP33     RGERVYVNISHPD-MVDFAR-GKTFFGAVMVG
hLT      QGDQLSTHT--DGIPHLVLSPSTVFFGAFAL
```

FIG. 14B

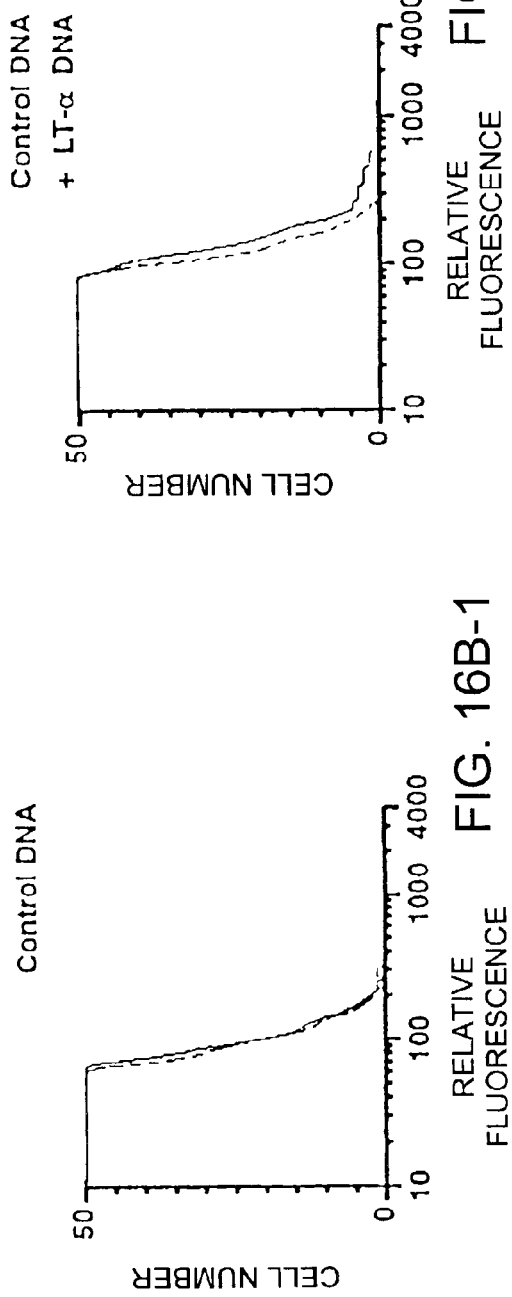

SEQUENCE LISTING

<160> NUMBER OF SEQ ID NOS: 23

<210> SEQ ID NO 1
<211> LENGTH: 726
<212> TYPE: DNA
<213> ORGANISM: Homo Sapien

<400> SEQUENCE: 1

```
ctggggctgg agggcagggg tgggaggctc caggggaggg gttccctcct gctagctgtg      60
gcaggagcca cttctctggt gaccttgttg ctggcggtgc ctatcactgt cctggctgtg     120
ctggccttag tgccccagga tcagggagga ctggtaacgg agacggccga ccccggggca     180
caggcccagc aaggactggg gtttcagaag ctgccagagg aggagccaga aacagatctc     240
agccccgggc tcccagctgc ccacctcata ggcgctccgc tgaagggggca ggggctaggc     300 tgggagacga cgaaggaaca ggcgtttctg acgagcggga cgcagttctc ggacgccgag     360
gggctggcgc tcccgcagga cggcctctat tacctctact gtctcgtcgg ctaccggggc     420
cgggcgcccc ctgcggcgg ggaccccag ggccgctcgg tcacgctgcg cagctctctg     480
taccgggcgg ggggcgccta cgggccgggc actcccgagc tgctgctcga gggcgccgag     540
acggtgactc cagtgctgga cccggccagg agacaagggt acgggcctct ctggtacacg     600
agcgtggggt tcggcggcct ggtgcagctc cggagggcg agagggtgta cgtcaacatc     660
agtcaccccg atatggtgga cttcgcgaga gggaagacct tctttggggc cgtgatggtg     720
gggtga                                                                 726
```

<210> SEQ ID NO 2
<211> LENGTH: 241
<212> TYPE: PRT
<213> ORGANISM: Homo Sapien

-continued

<400> SEQUENCE: 2

```
Leu Gly Leu Glu Gly Arg Gly Gly Arg Leu Gln Gly Arg Gly Ser Leu
  1               5                  10                  15
Leu Leu Ala Val Ala Gly Ala Thr Ser Leu Val Thr Leu Leu Leu Ala
             20                  25                  30
Val Pro Ile Thr Val Leu Ala Val Leu Ala Leu Val Pro Gln Asp Gln
         35                  40                  45
Gly Gly Leu Val Thr Glu Thr Ala Asp Pro Gly Ala Gln Ala Gln Gln
     50                  55                  60
Gly Leu Gly Phe Gln Lys Leu Pro Glu Glu Pro Glu Thr Asp Leu
 65                  70                  75                  80
Ser Pro Gly Leu Pro Ala Ala His Leu Ile Gly Ala Pro Leu Lys Gly
                 85                  90                  95
Gln Gly Leu Gly Trp Glu Thr Thr Lys Glu Gln Ala Phe Leu Thr Ser
            100                 105                 110
Gly Thr Gln Phe Ser Asp Ala Glu Gly Leu Ala Leu Pro Gln Asp Gly
        115                 120                 125
Leu Tyr Tyr Leu Tyr Cys Leu Val Gly Tyr Arg Gly Arg Ala Pro Pro
    130                 135                 140
Gly Gly Gly Asp Pro Gln Gly Arg Ser Val Thr Leu Arg Ser Ser Leu
145                 150                 155                 160
Tyr Arg Ala Gly Gly Ala Tyr Gly Pro Gly Thr Pro Glu Leu Leu Leu
                165                 170                 175
Glu Gly Ala Glu Thr Val Thr Pro Val Leu Asp Pro Ala Arg Arg Gln
            180                 185                 190
Gly Tyr Gly Pro Leu Trp Tyr Thr Ser Val Gly Phe Gly Gly Leu Val
        195                 200                 205
Gln Leu Arg Arg Gly Glu Arg Val Tyr Val Asn Ile Ser His Pro Asp
    210                 215                 220
Met Val Asp Phe Ala Arg Gly Lys Thr Phe Phe Gly Ala Val Met Val
225                 230                 235                 240
Gly
```

<210> SEQ ID NO 3
<211> LENGTH: 606
<212> TYPE: DNA
<213> ORGANISM: Homo Sapien

<400> SEQUENCE: 3

```
ctggccttag tgccccagga tcagggagga ctggtaacgg agacggccga ccccggggca    60
caggcccagc aaggactggg gtttcagaag ctgccagagg aggagccaga aacagatctc   120
agccccgggc tcccagctgc ccacctcata ggcgctccgc tgaagggcca ggggctaggc   180
tgggagacga cgaaggaaca ggcgtttctg acgagcggga cgcagttctc ggacgccgag   240
gggctggcgc tcccgcagga cggcctctat acctctact gtctcgtcgg ctaccggggc    300
cgggcgcccc ctggcggcgg ggaccccag ggccgctcgg tcacgctgcg cagctctctg    360
taccgggcgg ggggcgccta cgggccgggc actcccgagc tgctgctcga gggcgccgag   420
acggtgactc cagtgctgga cccggccagg agacaagggt acgggcctct ctggtacacg   480
agcgtggggt tcggcggcct ggtgcagctc cgagggggcg agagggtgta cgtcaacatc   540
agtcaccccg atatggtgga cttcgcgaga gggaagacct tctttggggc cgtgatggtg   600
gggtga                                                              606
```

<210> SEQ ID NO 4
<211> LENGTH: 201
<212> TYPE: PRT
<213> ORGANISM: Homo Sapien

<400> SEQUENCE: 4

```
Leu Ala Leu Val Pro Gln Asp Gln Gly Gly Leu Val Thr Glu Thr Ala
 1               5                  10                  15

Asp Pro Gly Ala Gln Ala Gln Gln Gly Leu Gly Phe Gln Lys Leu Pro
                20                  25                  30

Glu Glu Glu Pro Glu Thr Asp Leu Ser Pro Gly Leu Pro Ala Ala His
            35                  40                  45

Leu Ile Gly Ala Pro Leu Lys Gly Gln Gly Leu Gly Trp Glu Thr Thr
 50                  55                  60

Lys Glu Gln Ala Phe Leu Thr Ser Gly Thr Gln Phe Ser Asp Ala Glu
 65                  70                  75                  80

Gly Leu Ala Leu Pro Gln Asp Gly Leu Tyr Tyr Leu Tyr Cys Leu Val
                85                  90                  95

Gly Tyr Arg Gly Arg Ala Pro Pro Gly Gly Asp Pro Gln Gly Arg
            100                 105                 110

Ser Val Thr Leu Arg Ser Ser Leu Tyr Arg Ala Gly Gly Ala Tyr Gly
            115                 120                 125

Pro Gly Thr Pro Glu Leu Leu Leu Glu Gly Ala Glu Thr Val Thr Pro
130                 135                 140

Val Leu Asp Pro Ala Arg Arg Gln Gly Tyr Gly Pro Leu Trp Tyr Thr
145                 150                 155                 160

Ser Val Gly Phe Gly Gly Leu Val Gln Leu Arg Arg Gly Glu Arg Val
                165                 170                 175

Tyr Val Asn Ile Ser His Pro Asp Met Val Asp Phe Ala Arg Gly Lys
            180                 185                 190

Thr Phe Phe Gly Ala Val Met Val Gly
            195                 200
```

<210> SEQ ID NO 5
<211> LENGTH: 450
<212> TYPE: DNA
<213> ORGANISM: Homo Sapien

<400> SEQUENCE: 5

```
ccgctgaagg ggcagggggct aggctgggag acgacgaagg aacaggcgtt tctgacgagc      60
gggacgcagt tctcggacgc cgaggggctg cgctcccgc aggacggcct ctattacctc     120
tactgtctcg tcggctaccg gggccgggcg ccccctggcg gcgggaccc ccagggccgc      180
tcggtcacgc tgcgcagctc tctgtaccgg gcggggggcg cctacgggcc gggcactccc     240
gagctgctgc tcgagggcgc cgagacggtg actccagtgc tggaccccgg caggagacaa     300
gggtacgggc ctctctggta cacgagcgtg gggttcggcg gcctggtgca gctccggagg     360
gcgagaggg tgtacgtcaa catcagtcac cccgatatgg tggacttcgc gagagggaag     420
accttctttg gggccgtgat ggtgggggtga                                     450
```

<210> SEQ ID NO 6
<211> LENGTH: 149
<212> TYPE: PRT
<213> ORGANISM: Homo Sapien

<400> SEQUENCE: 6

-continued

```
Pro Leu Lys Gly Gln Gly Leu Gly Trp Glu Thr Thr Lys Glu Gln Ala
 1               5                  10                  15
Phe Leu Thr Ser Gly Thr Gln Phe Ser Asp Ala Glu Gly Leu Ala Leu
             20                  25                  30
Pro Gln Asp Gly Leu Tyr Tyr Leu Tyr Cys Leu Val Gly Tyr Arg Gly
         35                  40                  45
Arg Ala Pro Pro Gly Gly Asp Pro Gln Gly Arg Ser Val Thr Leu
 50                  55                  60
Arg Ser Ser Leu Tyr Arg Ala Gly Gly Ala Tyr Gly Pro Gly Thr Pro
 65              70                  75                  80
Glu Leu Leu Leu Glu Gly Ala Glu Thr Val Thr Pro Val Leu Asp Pro
                 85                  90                  95
Ala Arg Arg Gln Gly Tyr Gly Pro Leu Trp Tyr Thr Ser Val Gly Phe
             100                 105                 110
Gly Gly Leu Val Gln Leu Arg Arg Gly Glu Arg Val Tyr Val Asn Ile
             115                 120                 125
Ser His Pro Asp Met Val Asp Phe Ala Arg Gly Lys Thr Phe Phe Gly
 130                 135                     140
Ala Val Met Val Gly
 145
```

<210> SEQ ID NO 7
<211> LENGTH: 156
<212> TYPE: DNA
<213> ORGANISM: Homo Sapien

<400> SEQUENCE: 7

```
ctggccttag tgccccagga tcagggagga ctggtaacgg agacggccga ccccggggca    60
caggcccagc aaggactggg gtttcagaag ctgccagagg aggagccaga aacagatctc   120
agccccgggc tcccagctgc ccacctcata ggcgct                             156
```

<210> SEQ ID NO 8
<211> LENGTH: 52
<212> TYPE: PRT
<213> ORGANISM: Homo Sapien

<400> SEQUENCE: 8

```
Leu Ala Leu Val Pro Gln Asp Gln Gly Gly Leu Val Thr Glu Thr Ala
 1               5                  10                  15
Asp Pro Gly Ala Gln Ala Gln Gln Gly Leu Gly Phe Gln Lys Leu Pro
             20                  25                  30
Glu Glu Glu Pro Glu Thr Asp Leu Ser Pro Gly Leu Pro Ala Ala His
         35                  40                  45
Leu Ile Gly Ala
     50
```

<210> SEQ ID NO 9
<211> LENGTH: 17
<212> TYPE: DNA
<213> ORGANISM: Homo Sapien
<220> FEATURE:
<221> NAME/KEY: misc_feature
<222> LOCATION: 6
<223> OTHER INFORMATION: n = A,T,C or G

<400> SEQUENCE: 9

```
gtytcnggct cytcytc                                                   17
```

```
<210> SEQ ID NO 10
<211> LENGTH: 17
<212> TYPE: DNA
<213> ORGANISM: Homo Sapien
<220> FEATURE:
<221> NAME/KEY: misc_feature
<222> LOCATION: 6
<223> OTHER INFORMATION: n = A,T,C or G

<400> SEQUENCE: 10
gtytcnggtt cytcytc                                                  17

<210> SEQ ID NO 11
<211> LENGTH: 18
<212> TYPE: DNA
<213> ORGANISM: Homo Sapien

<400> SEQUENCE: 11
atgggggcac tggggctg                                                 18

<210> SEQ ID NO 12
<211> LENGTH: 19
<212> TYPE: DNA
<213> ORGANISM: Homo Sapien

<400> SEQUENCE: 12
gcggccgctt tagagcaca                                                19

<210> SEQ ID NO 13
<211> LENGTH: 27
<212> TYPE: DNA
<213> ORGANISM: Homo Sapien

<400> SEQUENCE: 13
gacagtgata ggcaccgcca gcaacaa                                       27

<210> SEQ ID NO 14
<211> LENGTH: 34
<212> TYPE: PRT
<213> ORGANISM: Homo Sapien
<220> FEATURE:
<221> NAME/KEY: VARIANT
<222> LOCATION: 7, 30, 31
<223> OTHER INFORMATION: Xaa = Any Amino Acid

<400> SEQUENCE: 14

Gly Leu Glu Gly Arg Gly Xaa Arg Leu Gln Gly Arg Gly Ser Leu Leu
 1               5                  10                  15

Leu Ala Val Ala Gly Ala Thr Gly Leu Val Thr Leu Leu Xaa Xaa Val
            20                  25                  30

Pro Ile

<210> SEQ ID NO 15
<211> LENGTH: 25
<212> TYPE: PRT
<213> ORGANISM: Homo Sapien

<400> SEQUENCE: 15

Leu Pro Glu Glu Glu Pro Glu Thr Asp Leu Ser Pro Gly Leu Pro Ala
 1               5                  10                  15

Ala His Leu Ile Gly Ala Pro Leu Lys
            20                  25

<210> SEQ ID NO 16
```

```
<211> LENGTH: 25
<212> TYPE: PRT
<213> ORGANISM: Homo Sapien
<220> FEATURE:
<221> NAME/KEY: VARIANT
<222> LOCATION: 1
<223> OTHER INFORMATION: Xaa = Any Amino Acid

<400> SEQUENCE: 16

Xaa Gln Ala Phe Leu Thr Ser Gly Thr Gln Phe Ser Asp Ala Glu Gly
 1               5                  10                  15

Leu Ala Leu Pro Gln Asp Gly Leu Tyr
            20                  25

<210> SEQ ID NO 17
<211> LENGTH: 8
<212> TYPE: PRT
<213> ORGANISM: Homo Sapien
<220> FEATURE:
<221> NAME/KEY: VARIANT
<222> LOCATION: 1, 5, 6
<223> OTHER INFORMATION: Xaa = Any Amino Acid

<400> SEQUENCE: 17

Xaa Gln Gly Leu Xaa Xaa Glu Thr
 1               5

<210> SEQ ID NO 18
<211> LENGTH: 5
<212> TYPE: PRT
<213> ORGANISM: Homo Sapien

<400> SEQUENCE: 18

Ser Ser Leu Tyr Arg
 1               5

<210> SEQ ID NO 19
<211> LENGTH: 26
<212> TYPE: PRT
<213> ORGANISM: Homo Sapien

<400> SEQUENCE: 19

Ala Gly Gly Ala Tyr Gly Pro Gly Thr Pro Glu Leu Leu Leu Leu Glu
 1               5                  10                  15

Gly Ala Glu Thr Val Thr Pro Val Leu Asp
            20                  25

<210> SEQ ID NO 20
<211> LENGTH: 233
<212> TYPE: PRT
<213> ORGANISM: Homo Sapien

<400> SEQUENCE: 20

Met Ser Thr Glu Ser Met Ile Arg Asp Val Glu Leu Ala Glu Glu Ala
 1               5                  10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80
```

```
Ser Arg Thr Pro Ser Asp Lys Pro Val Ala His Val Ala Asn Pro
            85                  90                  95
Gln Ala Glu Gly Gln Leu Gln Trp Leu Asn Arg Arg Ala Asn Ala Leu
            100                 105                 110
Leu Ala Asn Gly Val Glu Leu Arg Asp Asn Gln Leu Val Val Pro Ser
            115                 120                 125
Glu Gly Leu Tyr Leu Ile Tyr Ser Gln Val Leu Phe Lys Gly Gln Gly
    130                 135                 140
Cys Pro Ser Thr His Val Leu Leu Thr His Thr Ile Ser Arg Ile Ala
145                 150                 155                 160
Val Ser Tyr Gln Thr Lys Val Asn Leu Leu Ser Ala Ile Lys Ser Pro
                165                 170                 175
Cys Gln Arg Glu Thr Pro Glu Gly Ala Glu Ala Lys Pro Trp Tyr Glu
            180                 185                 190
Pro Ile Tyr Leu Gly Gly Val Phe Gln Leu Glu Lys Gly Asp Arg Leu
        195                 200                 205
Ser Ala Glu Ile Asn Arg Pro Asp Tyr Leu Asp Phe Ala Glu Ser Gly
    210                 215                 220
Gln Val Tyr Phe Gly Ile Ile Ala Leu
225                 230

<210> SEQ ID NO 21
<211> LENGTH: 260
<212> TYPE: PRT
<213> ORGANISM: Murinae gen. sp.

<400> SEQUENCE: 21

Met Ile Glu Thr Tyr Ser Gln Pro Ser Pro Arg Ser Val Ala Thr Gly
1               5                   10                  15
Leu Pro Ala Ser Met Lys Ile Phe Met Tyr Leu Leu Thr Val Phe Leu
            20                  25                  30
Ile Thr Gln Met Ile Gly Ser Val Leu Phe Ala Val Tyr Leu His Arg
        35                  40                  45
Arg Leu Asp Lys Val Glu Glu Glu Val Asn Leu His Glu Asp Phe Val
    50                  55                  60
Phe Ile Lys Lys Leu Lys Arg Cys Asn Lys Gly Glu Gly Ser Leu Ser
65                  70                  75                  80
Leu Leu Asn Cys Glu Glu Met Arg Arg Gln Phe Glu Asp Leu Val Lys
            85                  90                  95
Asp Ile Thr Leu Asn Lys Glu Glu Lys Lys Glu Asn Ser Phe Glu Met
            100                 105                 110
Gln Arg Gly Asp Glu Asp Pro Gln Ile Ala Ala His Val Val Ser Glu
        115                 120                 125
Ala Asn Ser Asn Ala Ala Ser Val Leu Gln Trp Ala Lys Lys Gly Tyr
    130                 135                 140
Tyr Thr Met Lys Ser Asn Leu Val Met Leu Glu Asn Gly Lys Gln Leu
145                 150                 155                 160
Thr Val Lys Arg Glu Gly Leu Tyr Tyr Val Tyr Thr Gln Val Thr Phe
                165                 170                 175
Cys Ser Asn Arg Glu Pro Ser Ser Gln Arg Pro Phe Ile Val Gly Leu
            180                 185                 190
Trp Leu Lys Pro Ser Ile Gly Ser Glu Arg Ile Leu Leu Lys Ala Ala
        195                 200                 205
Asn Thr His Ser Ser Ser Gln Leu Cys Glu Gln Gln Ser Val His Leu
    210                 215                 220
```

```
Gly Gly Val Phe Glu Leu Gln Ala Gly Ala Ser Val Phe Val Asn Val
225                 230                 235                 240

Thr Glu Ala Ser Gln Val Ile His Arg Val Gly Phe Ser Ser Phe Gly
                245                 250                 255

Leu Leu Lys Leu
        260
```

<210> SEQ ID NO 22
<211> LENGTH: 240
<212> TYPE: PRT
<213> ORGANISM: Homo Sapien

<400> SEQUENCE: 22

```
Gly Leu Glu Gly Arg Gly Gly Arg Leu Gln Gly Arg Gly Ser Leu Leu
1               5                   10                  15

Leu Ala Val Ala Gly Ala Thr Ser Leu Val Thr Leu Leu Ala Val
                20                  25                  30

Pro Ile Thr Val Leu Ala Val Leu Ala Leu Val Pro Gln Asp Gln Gly
            35                  40                  45

Gly Leu Val Thr Glu Thr Ala Asp Pro Gly Ala Gln Ala Gln Gln Gly
    50                  55                  60

Leu Gly Phe Gln Lys Leu Pro Glu Glu Pro Glu Thr Asp Leu Ser
65                  70                  75                  80

Pro Gly Leu Pro Ala Ala His Leu Ile Gly Ala Pro Leu Lys Gly Gln
                85                  90                  95

Gly Leu Gly Trp Glu Thr Thr Lys Glu Gln Ala Phe Leu Thr Ser Gly
            100                 105                 110

Thr Gln Phe Ser Asp Ala Glu Gly Leu Ala Leu Pro Gln Asp Gly Leu
        115                 120                 125

Tyr Tyr Leu Tyr Cys Leu Val Gly Tyr Arg Gly Arg Ala Pro Pro Gly
130                 135                 140

Gly Gly Asp Pro Gln Gly Arg Ser Val Thr Leu Arg Ser Ser Leu Tyr
145                 150                 155                 160

Arg Ala Gly Gly Ala Tyr Gly Pro Gly Thr Pro Glu Leu Leu Leu Glu
                165                 170                 175

Gly Ala Glu Thr Val Thr Pro Val Leu Asp Pro Ala Arg Arg Gln Gly
            180                 185                 190

Tyr Gly Pro Leu Trp Tyr Thr Ser Val Gly Phe Gly Gly Leu Val Gln
        195                 200                 205

Leu Arg Arg Gly Glu Arg Val Tyr Val Asn Ile Ser His Pro Asp Met
210                 215                 220

Val Asp Phe Ala Arg Gly Lys Thr Phe Phe Gly Ala Val Met Val Gly
225                 230                 235                 240
```

<210> SEQ ID NO 23
<211> LENGTH: 205
<212> TYPE: PRT
<213> ORGANISM: Homo Sapien

<400> SEQUENCE: 23

```
Met Thr Pro Pro Glu Arg Leu Phe Leu Pro Arg Val Cys Gly Thr Thr
1               5                   10                  15

Leu His Leu Leu Leu Leu Gly Leu Leu Leu Val Leu Leu Pro Gly Ala
                20                  25                  30

Gln Gly Leu Pro Gly Val Gly Leu Thr Pro Ser Ala Ala Gln Thr Ala
            35                  40                  45
```

```
Arg Gln His Pro Lys Met His Leu Ala His Ser Thr Leu Lys Pro Ala
    50              55                  60

Ala His Leu Ile Gly Asp Pro Ser Lys Gln Asn Ser Leu Leu Trp Arg
65              70                  75                      80

Ala Asn Thr Asp Arg Ala Phe Leu Gln Asp Gly Phe Ser Leu Ser Asn
            85                      90                  95

Asn Ser Leu Leu Val Pro Thr Ser Gly Ile Tyr Phe Val Tyr Ser Gln
            100             105             110

Val Val Phe Ser Gly Lys Ala Tyr Ser Pro Lys Ala Thr Ser Ser Pro
        115             120             125

Leu Tyr Leu Ala His Glu Val Gln Leu Phe Ser Ser Gln Tyr Pro Phe
    130             135             140

His Val Pro Leu Leu Ser Ser Gln Lys Met Val Tyr Pro Gly Leu Gln
145             150             155                     160

Glu Pro Trp Leu His Ser Met Tyr His Gly Ala Ala Phe Gln Leu Thr
            165             170             175

Gln Gly Asp Gln Leu Ser Thr His Thr Asp Gly Ile Pro His Leu Val
            180             185             190

Leu Ser Pro Ser Thr Val Phe Phe Gly Ala Phe Ala Leu
    195             200             205
```

LYMPHOTOXIN-β, LYMPHOTOXIN-β COMPLEXES, PHARMACEUTICAL PREPARATIONS AND THERAPEUTIC USES THEREOF

This application is a continuation of Ser. No. 08/466,254, filed Jun. 6, 1995 and now abandoned, which is a divisional of Ser. No. 08/222,614, filed Apr. 1, 1994 and now abandoned, which is a continuation of Ser. No. 07/990,304, filed Dec. 4, 1992 and now abandoned, which is a CIP of PCT/US91/04588 and a CIP of Ser. No. 07/544,862, filed Jun. 27, 1990 and now abandoned.

The invention described herein was made in part during the course of work under Grant No. CA 35638-07-10 from the National Institutes of Health. The U.S. Government has certain rights in this invention.

TECHNICAL FIELD OF THE INVENTION

This invention relates to lymphotoxin-β, a lymphocyte membrane-type polypeptide. Lymphotoxin-β, also referred to as p33, has been identified on the surface of T lymphocytes, T cell lines, B cell lines and lymphokine-activated killer cells.

This invention also relates to complexes formed between lymphotoxin-β (LT-β) and other lymphotoxin-type peptides such as lymphotoxin (which we refer to herein as "lymphotoxin-α (LT-α)" to distinguish it from LT-β) and to complexes comprising multiple subunits of LT-β. The LT-β polypeptide of this invention is expected to be useful in holding LT-α formed within the cell on the cell surface where either LT-β or the LT-α/LT-β complex may act as an inflammation regulating agent, a tumor growth inhibiting agent, a T cell inhibiting agent, a T cell activating agent, an immunomodulatory agent, an autoimmune disease regulating agent or an HIV regulating agent. Furthermore, the antitumor activity of the LT-α/LT-β complex may be delivered to tumor cells by tumor infiltrating lymphocytes (TILs) transfected with the gene for LT-β.

BACKGROUND OF THE INVENTION

The initiation of the immune response involves a complex array of intercellular signals. These signals typically involve soluble cytokines coupled with a number of cell-cell contact dependent signals. The contact dependent events, most notably activation of the T-cell receptor, lend specificity to the response whereas the soluble mediators are generally responsible for maintenance of cell differentiation and proliferation. Tumor Necrosis Factor (TNF) and LT-α are two polypeptides generally recognized for involvement with the initiation of the immune response.

TNF and LT-α are soluble proteins noted originally for their ability to inhibit the growth of tumors. [L. Old, "Tumor Necrosis Factor," *Science*, 230:630 (1985)]. Further research demonstrated that both proteins exhibit a wide range of activities. TNF is synthesized in response to various inflammatory insults by a variety of cell types including both hematopoietic and nonhematopoietic cells, while LT-α, in contrast, is made specifically by lymphocytes. The two known TNF receptors do not appear to discriminate between LT-α and TNF. [T. Schall et al., "Molecular Cloning and Expression of a Receptor for Human Tumor Necrosis Factor," *Cell*, 61:361–370 (1990); C. Smith et al., "A Receptor for Tumor Necrosis Factor Defines an Unusual Family of Cellular and Viral Proteins," *Science* 248:1019 (1990)]. In general, LT-α and TNF display similar spectra of activities in in vitro systems, although LT-α is often less potent. [J. Browning et al., Studies Of The Differing Affects Of Tumor Necrosis Factor And Lymphotoxin On The Growth Of Several Human Tumor Lines," *J. Immunol.*, 143:1859 (1989)].

TNF appears to play a major role in specific aspects of metabolic control, in the response to endotoxin shock, and in the regulation of hematopoietic cell development. [B. Beutler et al., "The History, Properties, and Biological Effects of Cachectin," *Biochemistry*, 27, (1988); M. Akashi et al., "Lymphotoxin: Stimulation And Regulation of Colony Stimulating Factors in Fibroblasts," *Blood*, 74:2383 (1989); G. Roodman et al., "Tumor Necrosis Factor-alpha and Hematopoietic Progenitors: Effects Of Tumor Necrosis Factor On The Growth Of Erythroid Progenitors CFU-E And BFU-E And The Hematopoietic Cell Lines k562, HL60, And HEL Cells," *Exp. Hematol.*, 15:928 (1987)].

Along with IL-1 and IL-6, TNF is also a major mediator of the inflammatory response. [D. Cavender et al., "Endothelial Cell Activation Induced By Tumor Necrosis Factor And Lymphotoxin," *Amer. Jour. Path.*, 134:551 (1989); R. Cotran et al., "Endothelial Activation Its Role In Inflammatory And Immune Reactions," in *Endothelial Cell Biology*, (Plenum Press, Simonescu & Simonescu, eds., 1988) 335]. TNF also appears to be involved in T cell activation under certain conditions. [M. Shalaby et al., "The Involvement Of Human Tumor Necrosis Factors-α And-β In The Mixed Lymphocyte Reaction," *J. Immunol.*, 141:499 (1988); N. Damle et al., "Distinct Regulatory Effects of IL-4 and TNF-α During CD3-Dependent and CD3-Independent Initiation Of Human T-Cell Activation," *Lymph. Res.*, 8:85 (1989); G. Ranges et al., "Tumor Necrosis Factor-α As A Proliferative Signal For An IL-2-Dependent T Cell Line: Strict Species Specificity of Action," *Amer. Assoc. Immunol.*, 142:1203 (1989); G. Ranges et al., "Tumor Necrosis Factor α/Cachectin Is A Growth Factor For Thymocytes," *J. Exp. Med.*, 167:1472 (1988); P. Scheurich et al., "Immunoregulatory Activity Of Recombinant Human Tumor Necrosis Factor (TNF)-α: Induction Of TNF Receptors On Human T Cells And TNF-α-Mediated Enhancement Of T Cell Responses," *J. Immunol.*, 138:1786 (1987)].

TNF is produced by several types of cells, including monocytes, fibroblasts, T cells and Natural Killer (NK) cells. [D. Goeddel et al., "Tumor Necrosis Factors: Gene Structure And Biological Activities," *Cold Spring Harbor Symposium Quant. Biol.*, 51, 597 (1986); D. Spriggs et al., "Tumor Necrosis Factor Expression In Human Epithelial Tumor Cell Lines," *J. Clin. Invest.*, 81:455 (1988); M. Turner et al., "Human T cells From Autoimmune and Normal Individuals Can Produce Tumor Necrosis Factor," *Eur. J. Immunol.*, 17:1807 (1987)]. Investigators have also detected murine and human forms of TNF that are associated with the surface of various cells either as a transmembrane protein or a receptor-bound molecule. [B. Luettig et al., "Evidence For the Existence of Two Forms of Membrane Tumor Necrosis Factor: An Integral Protein and a Molecule Attached To Its Receptor," *J. Immunol.*, 143:4034 (1989); M. Kriegler et al., "A Novel Form of TNF/Cachectin Is a Cell Surface Cytotoxic Transmembrane Protein: Ramifications For the Complex Physiology of TNF," *Cell*, 53, pp. 45–53 (1988); and M. Kinkhabwala et al., "A Novel Addition To the T Cell Repertory," *J. Exp. Med.*, 171:941–946 (1990)].

LT-α also has many activities, generally similar, but not identical to those of TNF, including tumor necrosis, induction of an antiviral state, activation of polymorphonuclear leukocytes, induction of class I major histocompatibility complex antigens on endothelial cells, induction of adhesion molecules on endothelium and growth hormone stimulation.

[N. Ruddle and R. Homer, "The Role of Lymphotoxin in Inflammation," *Prog. Allergy,* 40:162–182 (1988)]. Both LT-α and TNF are ligands to members of the nerve growth factor (NGF) receptor family. [S. Mallett and A. N. Barclay, "A New Superfamily Of Cell Surface Proteins Related To The Nerve Growth Factor Receptor," *Immunology Today,* 12:7:220–223 (1991).]

In contrast to TNF, LT-α secretion appears to be a specific property of only activated T cells and certain B-lymphoblastoid tumors. [N. Paul et al., "Lymphotoxin," *Ann. Rev. Immunol.,* 6:407 (1988)]. Some researchers have also indicated that a membrane-associated form of LT-α may be expressed on the surface of lymphocytes under certain circumstances [J. Hiserodt, et al., "Identification of Membrane-Associated Lymphotoxin (LT) On Mitogen-Activated Human Lymphocytes Using Heterologous Anti-LT Antisera In Vitro," *Cell. Immunol.,* 34:326–339 (1977); C. Ware et al., "Mechanisms of Lymphocyte-Mediated Cytotoxicity," *J. Immunol.,* 126:1927–1933 (1981); U. Anderson et al. *J. Immunol. Methods,* 123, 233 (1989); Y. Abe et al., *Jpn. J. Canc. Res.,* 82:23 (1991); Y. Abe et al., "Studies of Membrane Associated and Soluble (Secreted) Lymphotoxin In Human Lymphokine-Activated T-Killer Cells In Vitro," *Lymphokine and Cytokine Research,* 11, 2:15–121 (1992)].

In recent years genes for both TNF and LT-α have been isolated and cloned, leading to their complete characterization and to the availability of recombinant forms of both proteins. [P. Gray et al., "Cloning and Expression of cDNA For Human Lymphotoxin, A Lymphokine With Tumor Necrosis Activity," *Nature,* 312:121–124 (1984); D. Pennica et al., "Human Tumor Necrosis Factor: Precusor Structure, Expression And Homology To Lymphotoxin," *Nature,* 312:724 (1984)].

Other "cytokine-like" cell surface proteins including the CD40 protein have recently been shown to share certain similarities with TNF and LT-α. Like TNF and LT-α, the CD40 protein is a ligand to members of the TNF/nerve growth factor (NGF) receptor family. [S. Mallett and N. Barclay, *Immunology Today,* 12:220–223 (1991)]. The CD40 protein is a 277-amino acid protein expressed on the surface of B lymphocytes, epithelial cells, and some carcinoma cell lines. [R. Armitage et al., *Nature,* 357:80–82 (1992); T. Farrah and C. Smith, "Emerging Cytokine Family," *Nature,* 358:26 (1992)].

We have now identified a novel surface protein, lymphotoxin-β (LT-β) or p33. LT-β has been identified on the surface of several types of lymphocyte cells, including OKT3-stimulated primary T cells, antigen specific IL-2 dependent CTL clones, and a PMA-stimulated human T cell hybridoma II-23.D7. LT-β targets LT-α produced in the cell to the cell membrane where LT-β and LT-α appear as a complex (designated "LT-α/LT-β" throughout this disclosure). The LT-α/LT-β complex is believed to be a novel mechanism for membrane expression of LT-α by activated T-cells. [Androlewicz et al., "Lymphotoxin Is Expressed As a Heteromeric complex With A Distinct 33 kDa Glycoprotein On The Surface Of An Activated Human T Cell Hybridoma," *Journal Of Biological Chemistry,* 267:2542–2547 (1992)]. The LT-α/LT-β complex may exhibit cytolytic and cell regulatory activity similar to the soluble LT-α, TNF and CD40 proteins. The membrane-associated LT-β complexed with LT-α may represent, as a complex, a novel ligand for T cell interactions with other cells and may also be useful in targeted cell lysis.

SUMMARY OF THE INVENTION

The novel protein of the present invention has been named lymphotoxin-β (LT-β). This protein is found on the surface of several types of lymphocyte cells, including OKT3-stimulated primary T cells, antigen-specific IL-2 dependent CTL clones, and a PMA-stimulated human T cell hybridoma, II-23.D7. It forms a novel complex with LT-α and forms complexes with other LT-β subunits (e.g., (LT-β)$_2$ LT-α complexes).

LT-β has a molecular weight of 31–35 kD as determined by immunoprecipitation and SDS-PAGE. LT-β exhibits N-linked glycosylation. The amino acid sequence of lymphotoxin-β is set forth in SEQ ID NO:2, and the amino acid sequences of several soluble lymphotoxin-β peptides are set forth in SEQ ID NO:4, SEQ ID NO:6 and SEQ ID NO:8. The DNA sequence coding for lymphotoxin-β is set forth in SEQ ID NO:1 and DNA sequences coding for several soluble lymphotoxin-β peptides are set forth in SEQ ID NO:3, SEQ ID NO:5, and SEQ ID NO:7.

LT-β as a cell membrane protein binds LT-α during synthesis, thus "targeting" the LT-α to the cell membrane. In the absence of LT-β, LT-α is secreted into the extracellular medium. The LT-α/LT-β complex is recognized by polyclonal antisera raised against recombinant lymphotoxin-α (rLT-α) expressed in CHO cells or by monoclonal antibodies (mAbs) raised against natural LT-α. Furthermore, antisera that recognize the LT-α/LT-β complex and (LT-α)$_3$ block the mixed lymphocyte reaction (MLR), a standard immunological assay of the expected proliferative response of T lymphocytes to allogenic stimulation, i.e., the introduction of T lymphocytes from another individual, which are recognized as foreign (non-self) by the "responder" lymphocytes. [See, e.g., M. Shalaby et al., *J. Immunol.,* 141:499 (1988)].

The LT-β protein was purified by affinity chromatography, partially sequenced and a specific oligonucleotide probe was designed. The cDNA encoding the LT-β was isolated by probing a cDNA library from activated II-23.D7 cells, a human T-cell hybridoma that displays large amounts of surface lymphotoxin upon phorbol ester activation. The identified amino acid sequence encodes a 240–244 amino acid sequence (a molecular mass of the unmodified protein of about 25130–25390 kDa). See SEQ ID NO:2. The amino acid sequence and the placement of the transmembrane region are typical of a type II membrane protein.

This sequence comprises a short 14–18 amino acid N-terminal "cytoplasmic" domain. Following this cytoplasmic domain there is an extensive stretch of 30 hydrophobic amino acids which presumably acts as a membrane anchoring domain. No identical sequences were found within available databases. There is one cysteine residue in the extracellular domain and two methionines within the last C-terminal 17 amino acids. This is consistent with the very limited cyanogen bromide cleavage pattern exhibited by this protein.

Comparison of the LT-β sequence with other proteins known to bind to members of the TNF/NGF receptor family reveals considerable structural similarity. Four of the ligands to members of the TNF/NGF receptor family (TNF, LT-α, LT-β and the CD40 ligand) resemble type II membrane proteins and share at least four regions of sequence conservation in the extracellular domain as indicated in FIG. 14. The conserved TNF and LT-α domains shared with LT-β are likely to be involved in intersubunit interactions and β sheet organization. These regions of conservation can account for the association between LT-α and LT-β. The existence of these homology regions may facilitate engineering the polypeptide to form complexes with, for example, TNF or the CD40 ligand. Such a molecule would have mixed functions and could possibly be used as a custom designed drug. [See J. Fuh et al., "Rational Design Of Potent Antagonists To The Human Growth Hormone Receptor," *Science*, 256:1677 (1992)].

We believe that the polypeptide complexes of this invention are important in T cell activation events and are useful in compositions and methods for T cell activation or T cell suppression and as therapeutic agents in the treatment of inflammation or applications requiring cytolytic activities, such as inhibition of tumor cell or neoplasia growth. We also believe that the polypeptide complexes may be important in cellular immunotherapies, including enhancing the tumoricidal properties of tumor infiltrating lymphocytes in Tumor Infiltrating Lymphocyte ("TIL") therapy. TIL immunotherapy may be improved by gene transfer techniques. For example, a gene may be added to tumor cells for the purpose of inducing the body's immune system to mediate an effective tumor-directed immune response. [See, e.g., W. F. Anderson, "Human Gene Therapy." *Science*, 256:808–813 (1992)].

We also believe, based upon similarities between a molecule identified as "Fas" and members of the TNF/NGF receptor family, that the polypeptide complexes of this invention may be involved in the internal cell process known as programmed cell death or apoptosis, and may therefore be involved in mediating autoimmune disease. [See, e.g., N. Itoh et al., "The Polypeptide Encoded By The cDNA For Human Cell Surface Antigen Fas Can Mediate Apoptosis," *Cell*, 66:233–243 (1991); R. Watanabe-Fukunaga et al., "Lymphoproliferation Disorder In Mice Explained By Defects In Fas Antigen That Mediates Apoptosis," *Nature* 356:314 (1992)].

Antibodies to LT-β, its related polypeptides, the LT-α/LT-β complex or the other polypeptide complexes of this invention may also disrupt critical LT interactions with particular receptors, thus specifically affecting LT-mediated events other than those mediated through the known TNF receptor forms. Likewise, receptors for TNF, LT-α or LT-α/LT-β, or their derivatives (e.g., soluble receptors and IgG/receptor fusion proteins) may be used to inhibit the polypeptides and complexes of this invention.

BRIEF DESCRIPTION OF THE DRAWINGS

FIG. 4 shows two autoradiographs (A and B) depicting immunoprecipitation of $^{125}$I-labeled surface proteins from PMA-activated II-23.D7 cells.

FIG. 6 depicts affinity purification 1-D CNBr peptide mapping of those proteins from PMA-activated II-23.D7 cells recognized by anti-rLT-α serum. FIG. 6A shows the ~33 kD and ~20 kD protein bands did not bind to an affinity column prepared using preimmune serum (PRE) but did bind to an affinity column prepared using anti-rLT-α antiserum (POST).

FIG. 13 depicts amino acid sequence of LT-β fragments obtained by direct N-terminal sequencing and in situ trypsin digestion followed by reverse phase HPLC resolution of the digested peptides.

FIG. 14 depicts an amino acid sequence comparison of four members of the family of ligands binding to members of the TNF/NGF-receptor family. Homology regions are shown in bold type face with sequence identity indicated with a dot and conserved sequences with an asterisk. Putative N-linked glycosylation sites are boxed.

FIG. 16 depicts expression of LT-α and LT-β in CHO cells. A) FACS analysis of CHO cells transiently transfected with the LT-β cDNA. Either parental dHFR-CHO or LT-α expressing CHO cells were electroporated with either pCDM8 containing an irrelevant insert (clone 4) or the pCDM8/LT-β plasmid and stained with control IgG( - - - ) or anti LT-α monoclonal antibodies (_____). B) Panel B depicts expression of LT-α and LT-β in COS cells. Cells were transfected with control DNA or the pCDM8/LTβ plasmid, either with or without pCDM8/LTα and stained as per panel A.

DETAILED DESCRIPTION OF THE INVENTION

Figure 1A:
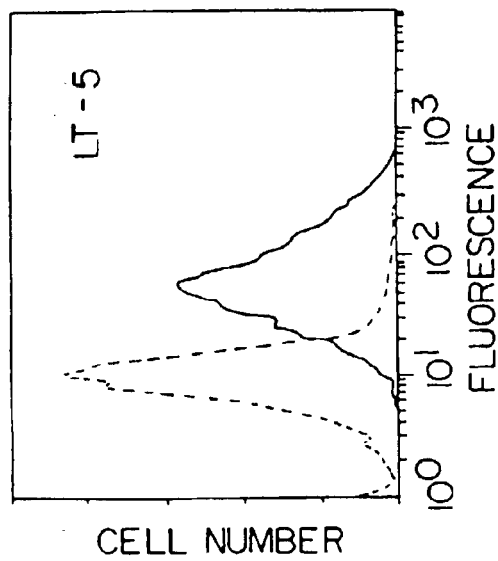
FIG. 1 depicts flow cytofluorometric analysis of OKT3-stimulated, IL-2 expanded peripheral blood lymphocytes (PBL) showing reaction with 3 different rabbit anti-rLT-α antisera and showing essentially no reaction with rabbit anti-rTNF antisera.
Figure 1B:
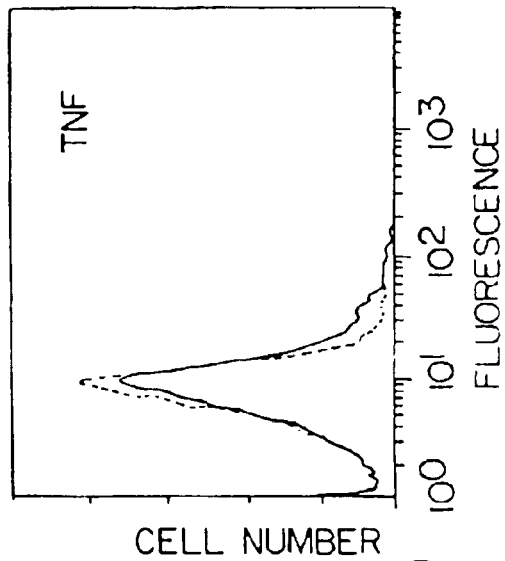
Figure 1C:
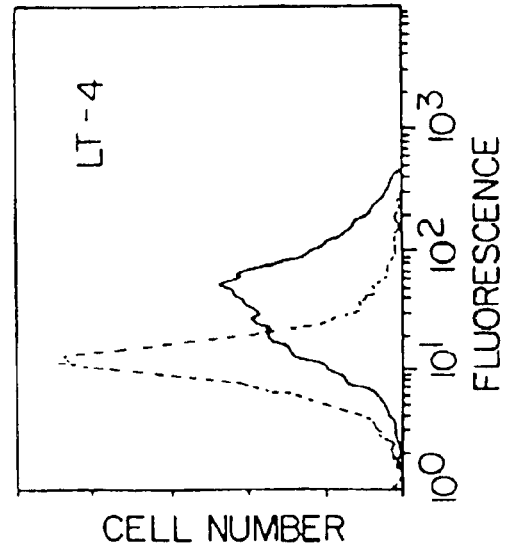
Figure 1D:
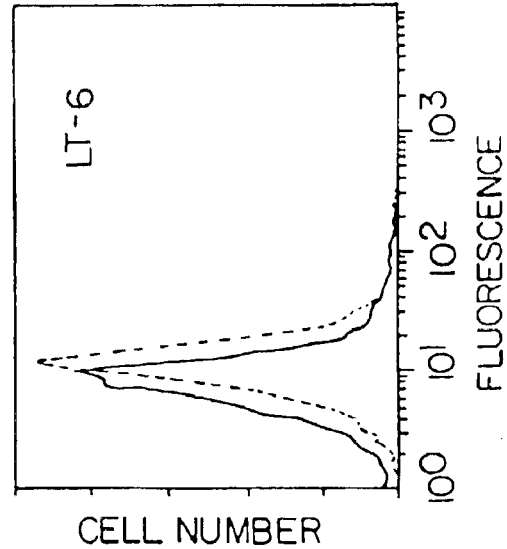

In order that the invention herein described may be fully understood, the following detailed description is set forth.

This invention relates to lymphotoxin-β, a lymphocyte membrane-type polypeptide. The amino acid sequence of lymphotoxin-β is set forth in SEQ ID NO:2.

This polypeptide, also referred to as p33, has a molecular weight of 31 to 35 kD. The polypeptides of this invention may be associated with a cell surface or not associated with such a surface.

This invention also relates to soluble forms of lymphotoxin-β. Soluble lymphotoxin-β peptides are defined by the amino acid sequence of lymphotoxin-β wherein the sequence is cleaved at any point between the end of the transmembrane region (i.e., at about amino acid #44) and the first homology region at about amino acid #95. Amino acid sequences of two soluble lymphotoxin-β peptides are defined by SEQ ID NO:4 and SEQ ID NO:6. Several additional soluble lymphotoxin-β polypeptides comprise the amino acid sequence as defined by SEQ ID NO:6 with additional amino acid residues at the 5' end. The additional residues may comprise the 52 amino acid residues as defined by SEQ ID NO:8. The soluble lymphotoxin may also comprise an amino acid sequence defined by SEQ ID NO:6 plus a portion of SEQ ID NO:8 comprising 1 to 51 of the amino acid residues beginning from the 3' end. Such soluble peptides may include any number of well known leader sequences at the 5' end. Such a sequence would allow the peptides to be expressed in a eukaryotic system. [See, e.g., Ernst et al. U.S. Pat. No. 5,082,783 (1992)].

The polypeptide complexes of this invention comprise a first polypeptide comprising an amino acid sequence selected from the group of SEQ ID NO:2, SEQ ID NO:4, SEQ ID NO:6, and the sequence defined by SEQ ID NO:6 plus the entirety or a portion of SEQ ID NO:8 as described above, complexed with a second polypeptide selected from the same group and/or with a second polypeptide such as: lymphotoxin-α, native human or animal lymphotoxin-α, recombinant lymphotoxin-α, soluble lymphotoxin-α, secreted lymphotoxin-α, or lymphotoxin-α-active fragments of any of the above.

The novel LT-β peptide forms a complex with LT-α and forms complexes with other LT-β subunits (e.g., (LT-β)$_2$ LT-α complexes). These complexes may be cell associated or not associated with a cell, and may complex with other type II membrane proteins sharing common homology regions as described above.

The polypeptide complexes are recognized by polyspecific antisera that recognize recombinant LT-α, suggesting that the complex exhibits LT-α epitopes. These antisera include a commercial anti-LT-α monoclonal antibody (Boehringer Mannheim), and polyspecific antisera raised against recombinant lymphotoxin-α (rLT-α) expressed in transfected Chinese Hamster Ovary (CHO) cells. Polyclonal antisera that recognize these complexes also block the mixed lymphocyte reaction (MLR), but a monoclonal anti-rLT-α antibody that recognizes soluble LT-α do not block the MLR. The complexes of the present invention thus appear to play an important role in T cell activation. We also expect these complexes to have T cell regulatory activities and cytotoxic activities similar to those of soluble LT-α or TNF.

This invention also relates to DNA consisting essentially of DNA sequences that code for the polypeptides comprising the amino acid sequences described above, recombinant DNA molecules characterized by that DNA, hosts selected from the group of unicellular hosts or animal and human cells in culture transfected with that DNA, and recombinant methods of using that DNA and those recombinant DNA molecules and hosts to produce the polypeptides coded thereby.

More specifically, this invention relates to an isolated DNA sequence comprising the nucleotide sequence as defined by SEQ ID NO:1.

This invention also relates to polypeptides encoded by that sequence, DNA sequences that hybridize with that DNA sequence that code for a polypeptide that is substantially homologous with lymphotoxin-β, and degenerate DNA sequences comprising nucleotide sequences that code for lymphotoxin-β.

This invention also relates to DNA sequences that code for soluble lymphotoxin-β peptides. These DNA sequences are defined by SEQ ID NO:3 and SEQ ID NO:5. This invention also relates to several additional soluble lymphotoxin-β peptides that are coded for by the DNA of SEQ ID NO:5 plus several additional nucleotide triplets at the 5' end. The additional nucleotide triplets may comprise the 52 triplets as defined by SEQ ID NO:7. The soluble lymphotoxin peptide may also be encoded by SEQ ID NO:5 plus a portion of SEQ ID NO:7 comprising 1 to 51 nucleotide triplets beginning from the 3' end.

This invention also relates to DNA sequences that hybridize to any of the sequences identified above that code on expression for lymphotoxin-β or soluble lymphotoxin-β peptides. This invention also relates to degenerate nucleotide sequences that code for lymphotoxin-β or a soluble lymphotoxin-β peptide, and to DNA sequences that code for polypeptides that are substantially homologous with a soluble lymphotoxin-β peptide.

Lymphotoxin-β was identified, isolated and characterized using the techniques described below:

Flow Cytofluorometric Analysis

First we demonstrated the expression of LT-α epitopes on the surface of T cells using flow cytofluorometric analysis. We observed that human peripheral blood mononuclear cells activated with OKT3 monoclonal antibody demonstrated expression of LT-α epitopes by reacting with anti-rLT-α antisera. Only anti-rLT-α antisera, not anti-rTNF antisera, bound to OKT3-stimulated primary T cells.

We also observed that a human T cell hybridoma, II-23.D7 [C. Ware et al., "Human T Cell Hybridomas Producing Cytotoxic Lymphokines: Induction of Lymphotoxin Release And Killer Cell Activity By Anti-CD3 Monoclonal Antibody Or Lectins And Phorbol Ester," *Lymph. Res.*, 5:313 (1986)], secreted LT-α upon PMA stimulation and also expressed surface LT-α-related epitopes upon PMA stimulation. We also demonstrated that PMA-activated II-23.D7 cells were able to remove LT-neutralizing antibodies from the rabbit anti-rLT-α antisera, while control U937 cells, which lack all surface LT-α forms, were not. We further ruled out the possibility that the rabbit anti-rLT-α antisera had bound (complexed) with rabbit LT-α (the resulting complexes subsequently binding to cellular LT-α/TNF receptors on the II-23.D7 cells) by saturating the cellular receptors with excess soluble TNF or LT-α and observing that this had no effect on the staining. These assays demonstrate that the LT-α-related epitopes on this hybridoma are genuinely related to LT-α.

We also observed that pretreatment of the antisera with excess rLT-α blocked the ability of the antisera to stain II-23.D7 cells, while pretreatment with rTNF had no effect. This assay demonstrated the specificity of the antisera for LT-α-related epitopes.

Trypsinization of the stimulated II-23.D7 cells prior to staining led to loss of the signal, demonstrating that the epitopes recognized by the antisera were proteins.

We also demonstrated that CHO-derived contaminants did not contribute to the antisera recognition of induced proteins on the surface of activated II-23.D7 cells by showing that CHO cells stably transfected with the LT-α gene, which produce only soluble LT-α, were not stained by the anti-LT-α antisera.

Immunoprecipitation

We further characterized these surface LT-α-related proteins by either surface iodination ($^{125}$I-labelling) or metabolic labelling ($^{35}$S-Met or $^{35}$S-Cys) of PMA-activated II-23.D7 cells, followed by solubilization of the plasma membrane with detergent and immunoprecipitation of the labeled LT-α-related proteins.

Surface iodination coupled with immunoprecipitation revealed two proteins recognized by the anti-LT-α antisera: a 25–26 kD form subsequently referred to as LT-α, and a 31–35 kD form subsequently referred to as LT-β or p33. We observed that neither the preimmune serum from the same rabbit nor anti-rTNF rabbit serum immunoprecipitated these bands from the iodinated, PMA-activated II-23.D7 cells. One dimensional partial CNBr peptide mapping of the iodinated, immunoprecipitated bands showed that the 25–26 kD form (LT-α) cleaves in a pattern identical to that of iodinated recombinant LT-α, reinforcing the correlation between surface LT-α and soluble LT-α. The iodinated 31–35 kD form (LT-β, or p33) was not cleaved by CNBr, indicating that it is distinct from the known LT-α gene product.

We further characterized the LT-α and LT-β proteins by metabolic labelling of PMA-activated II-23.D7 cells with $^{35}$S-methionine or $^{35}$S-cysteine, followed by immunoprecipitation. The distribution of cysteine and methionine provides a means of distinguishing between TNF and LT-α and between forms of each with and without their signal sequences [M. Kriegler et al., *Cell*, 53:45 (1988)]. Secreted TNF contains cysteine, but not methionine, while secreted LT-α contains only methionine and no cysteine residues. LT-α, however, has one cysteine residue in its signal sequence, while TNF contains two methionine residues in its signal sequence.

We labeled separate cultures of PMA-treated II-23.D7 cells with either $^{35}$S-methionine or $^{35}$S-cysteine and precipitated immunoreactive proteins from the culture media and the cells. Subsequent SDS-PAGE analysis of the immunoprecipitates from the culture media of cells labeled with $^{35}$S-methionine revealed a 25 kD form of LT-α while the immunoprecipitates from the culture media of cells labeled with $^{35}$S-cysteine did not, a pattern expected for secreted LT-α. Analysis of the washed cells showed both the 25–26 kD LT-α form and the 33 kD LT-β form. These results parallelled the membrane-associated forms observed using surface iodination.

The 25–26 kD LT-α lacked cysteine, indicating processing of the leader sequence. We also observed that the 33 kD LT-β incorporated both $^{35}$S-methionine and $^{35}$S-cysteine, distinguishing itself as different from the 25 kD LT-α form. Typically, LT-α bound to its receptor can be cross-linked to the receptor using a chemical linker such as BOSCOES (i.e., (bis[2-[succinimidooxy-carbonyloxy]ethyl] sulfone; Pierce, Rockford, Ill.). [J. S. Andrews et al., "Characterization of the Receptor for Tumor-Necrosis Factor (TNF) and Lymphotoxin (LT) on Human T Lymphocytes," *J. Immunol.*, 144:2582 (1990)]. We observed that when surface iodinated II-23.D7 cells were treated with a cross-linking agent, there was no association of either the 25–26 kD LT-α or the 33 kD LT-β related form with an additional membrane protein. This assay demonstrated that receptor binding is not the mechanism by which LT-α and LT-β remain associated with the cell membrane. Sequence analysis of LT-β showed no relationship to either of the two TNF-receptor forms [C. Smith et al., *Science*, 248:1019 (1990); T. J. Schall et al., *Cell*, 61:61 (1990)].

Affinity Chromatography

Further characterization of the LT-β and LT-α proteins on the surface of II-23.D7 cells was obtained through affinity chromatography. We observed that LT-α/LT-β complex on the surface of PMA-treated II-23.D7 cells bound to lentil lectin, indicating a glycoprotein structure for each form. Hence a lentil lectin chromatography step was used as a purification step prior to antisera affinity chromatography. We bound detergent-solubilized PMA-treated II-23.D7 proteins to lentil lectin sepharose and eluted with α-methyl mannoside. We prepared both control IgG and anti-LT-α-IgG affinity columns to accurately assess those proteins specifically recognized by the anti-LT-α antiserum. We then applied the proteins that bound to lentil lectin to these columns. We observed that low pH elution of the columns led to the release of the LT-β and LT-α proteins from the anti-LT-α affinity column. SDS-PAGE analysis of the eluate closely resembled the SDS-PAGE analysis of immunoprecipitated proteins from surface iodinated PMA-treated II-23.D7 cells. This comparison demonstrated that similar proteins were purified by the two methods.

We observed that during affinity purification, the ⁻25 kD LT-α form appeared to be cleaved to a 19–20 kD form, or a "des 20" form. The original isolation of natural LT-α from the RPMI 1788 tumor cell line [B. Aggarwal et al., "Primary Structure of Human Lymphotoxin Derived From 1788 Lymphoblastoid Cell Line," *J. Biol. Chem.*, 260:2334–2344 (1985)] also yielded an N-terminally cleaved 20 kD LT-α form. One of the methionines is lost in this "des-20" natural LT-α form, producing a different CNBr cleavage pattern from the intact molecule. One-dimensional CNBr digests of the affinity-purified LT-α protein demonstrated a cleavage pattern that is consistent with the truncated natural LT-α form, and we concluded that the affinity-purified "des-20" LT-α form probably results from a similar cleavage as observed with the natural LT-α "des-20" form.

We further observed that LT-β generates a doublet upon partial CNBr cleavage. The cleavage pattern generated by the LT-β protein demonstrated that methionine residue(s) were present, and at least one methionine was within 5–20 residues from either the C- or N-terminus (methionine residues within 1–5 residues of either end would not be detected when cleaved using this mapping technique). This pattern suggested that LT-β does not contain the entire known LT-α sequence.

We observed that the LT-β protein is also expressed by antigen-activated primary cytotoxic T lymphocyte clones. Metabolic labelling of these cells followed by immunoprecipitation with anti-rLT-α revealed LT-β along with small amounts of LT-α. These results demonstrated that LT-β is made by primary T cells as well as by the II-23.D7 hybridoma.

Initial Purification of the LT-β and LT-α Proteins

We purified these LT-α and LT-β proteins using the following general steps. We first added phorbol myristic acetate (PMA) to II-23.D7 cells. After 24 hours we harvested the cells and washed them with cold serum-free RPMI medium. To the chilled cell pellet we added ice-cold lysis buffer (HEPES, NP-40, EDTA, NaCl, and sodium azide) to which benzamidine, phenyl methyl sulfonyl chloride (PMSF), and N-ethyl maleimide (NEM), soybean trypsin inhibitor, pepstatin and aprotinin had been freshly added. We homogenized the cells gently in a Dounce homogenizer and centrifuged the lysate. We centrifuged and collected the supernatant. We loaded the supernatant onto a lentil-lectin sepharose column equilibrated in lysis buffer to which we had added $CaCl_2$ and $MnCl_2$. We washed the column with lysis buffer with $CaCl_2$ and $MnCl_2$ and then eluted with lysis buffer containing α-methyl mannoside. We pooled the eluate fractions and loaded directly onto a rabbit nonspecific IgG sepharose affinity column which was directly connected to a rabbit anti-rLT-α sepharose affinity column. We washed both columns with the same lysis buffer with EDTA followed by lysis buffer wherein the NP-40 had been replaced with MEGA-8 (Octanoyl-N-methyl glucamide, Boehringer-Mannheim). We eluted the washed columns individually with a solution of 5 mM MEGA-8, 50 mM glycine, NaCl, benzarnidine, and EDTA as described in Browning et al., "Lymphotoxin And An Associated 33-kDa Glycoprotein are Expressed On The Surface Of An Activated Human T-Cell Hybridoma," *J. Immunol.* 147:1230–1237 (1991). The first fractions following the pH shift were pooled, lyophilized and resuspended in water with SDS, and dialyzed against a solution of HEPES and SDS. We dried the dialyzed fractions on a speed-vac and resuspended in water. We mixed aliquots with Laemmli loading buffer and electrophoresed on SDS-PAGE. We visualized proteins by silver staining.

We observed that LT-α epitope(s) are present on the surface of the II-23.D7 T cell hybridoma only following cell activation such as occurs with PMA treatment. In contrast, when present on primary T-cells, PMA treatment leads to loss of the surface antigen. Additionally, we found that rabbit polyclonal antisera to either recombinant LT-α (produced in CHO cells) or natural LT-α (e.g., Genzyme, Boston, Mass.) recognized the LT-α epitope(s).

We have also observed that our antisera recognizing the LT-α/LT-β complex blocks the MLR, whereas a particular monoclonal antibody recognizing a soluble LT-α does not [M. Shalaby et al., *J. Immunol.*, 141:499 (1988)]. The LT-α/LT-β complex of the invention, therefore, may be a mediator in T cell activation.

The presence of LT-β with LT-α in immunoprecipitates from cell lysates suggested that either LT-β is antigenically related to LT-α or that LT-β is bound to LT-α or both. To address this issue 25 kD and 33 kD bands from $^{35}$S-methionine labeled cells were immunoprecipitated with rabbit polyclonal anti-rLT-α serum, eluted from excised gel slices and subjected to reimmunoprecipitation with either anti-rLT-α polyclonal serum or anti-rLT-α mAb. LT-α, but not LT-β, could be immunoprecipitated with either of the anti-rLT-α antibodies, suggesting that LT-β is not antigenically related to LT-α. These observations indicated that LT-β is physically associated with LT-α.

Figure 9A:
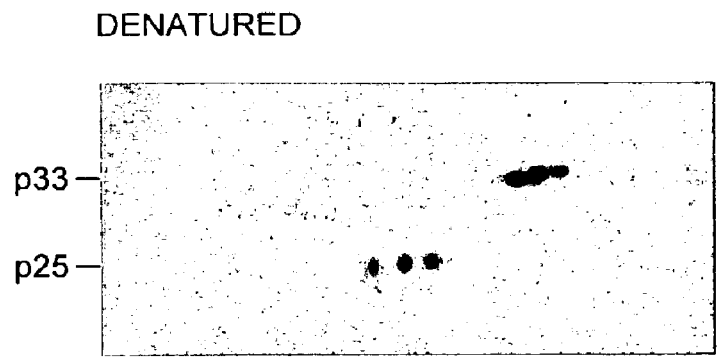
FIG. 9 (comprising parts 9A and 9B) shows the results of isoelectric focusing under denaturing conditions of the immunoprecipitated p33 (LT-β) and p25 (LT-α) proteins.
Figure 10A:
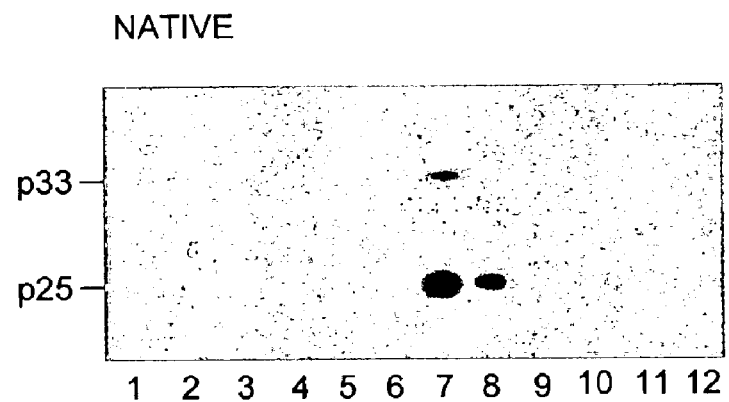
FIG. 10 (comprising parts 10A and 10B) shows the results of isoelectric focusing under native conditions of the immunoprecipitated p33 (LT-β) and p25 (LT-α) proteins. Together FIGS. 9 and 10 indicate that LT-β and LT-α form a denaturable complex.

To further investigate the hypothesis that surface LT-α and LT-β form a complex, we performed isoelectric focusing (IEF) experiments under both denaturing and native conditions, the rationale being that if LT-α and LT-β are physically associated, then they should focus as a complex under native conditions but as separate entities under denaturing conditions. The individual isoelectric points (pI's) for LT-α and LT-β were determined by two-dimensional gel analysis (denaturing conditions) (FIG. 9A). LT-α possesses five charged isomers ranging in pI from 6.5 to 7.3, whereas LT-β possesses four charged isomers ranging in pI from 5.5 to 6.0. When focusing was performed under native conditions, however, LT-α and LT-β focused together as a broad band ranging in pI from 6.3 to 7.2 (FIG. 10A, lanes 6–8). Therefore, the migration of LT-β was significantly retarded under native conditions.

Further Purification and Identification of LT-α and LT-β

We later purified these LT-α and LT-β proteins using the following general steps. We grew II-23.D7 cells in RPMI medium with fetal bovine serum and we harvested the cells from 50 l of RPMI and resuspended them in medium and we added phorbol myristoyl acetate (PMA). After activation for 6 hours, we harvested the cells by centrifugation and washed them with Dulbecco's phosphate buffered saline. We suspended the final cell pellet in cold lysis buffer and passed the pellet once through a nitrogen cavitator. We centrifuged the lysed cells and discarded the supernatant. We extracted the pellet overnight in lysis buffer with detergent and then centrifuged it again.

We added the supernatant containing the detergent solubilized membranes to affinity resin composed of monoclonal anti-LT-α coupled to Affi-gel (10) and rocked the suspension overnight. We collected the resin into a small column and washed it with HEPES with nonidet P40, and then with the same buffer with 1% w/v MEGA-8, we eluted the bound proteins with MEGA-8 in glycine buffer and neutralized the fractions immediately with Tris base. We determined the presence of LT-β and LT-α in the fractions by SDS-PAGE analysis and silver staining. We pooled fractions containing these proteins and added SDS, and we dialyzed the pool against 0.1× laemmli sample buffer (using multiple changes to remove the MEGA-8 detergent). We lyophilized the dialyzed solution to dryness and resuspended it in ⅒th the original volume of water.

We ran the sample on an SDS-PAGE gel, blotted onto a ProBlot membrane and stained with Coomassie blue dye. We excised the LT-β and LT-α bands and loaded them into a protein sequencer. We obtained the N-terminal sequence by Edman degradation. We found the sequence of the membrane associated LT-α band to exactly match that described for secreted LT-α, i.e., Leu Pro Gly Val Gly Leu Thr Pro Ser (amino acid No. 1 to 9.) [P. Gray et al., *Nature*, 312:121–124 (1984)]. The Edman degradation analysis revealed that the N-terminal portion of the associated LT-β protein included two possible amino acid sequences: Gly Leu Glu Gly Arg Gly Gin Arg Leu Gln or Gly Leu Glu Gly Arg Leu Gln Arg Leu Gin. Subsequent DNA analysis using more accurate cDNA techniques confirmed that the correct sequence was Gly Leu Glu Gly Arg Gly Gly Arg Leu Gln.

In each case where a surface LT-α form was detected, we were also able to detect LT-β (i.e., in PMA-activated II-23.D7, activated CTL clones, and Hut-78 cells constitutively expressing a surface LT-α form). Because LT-α is secreted from transfected CHO cells in the absence of a surface LT-α form, and because the presence of LT-β is associated with surface-bound LT-α, we concluded that LT-β complexes with LT-α to target it to the cell surface. Biochemically, LT-β and LT-α co-migrate on a non-denaturing isoelectric focusing gel, but when the complex is dissociated with urea, the two proteins run separately. [See FIGS. 9A, 10A.] These observations have led us to conclude that LT-α and LT-β exist as a complex on the cell surface.

Identifying DNA Sequences that Code for Lymphotoxin-β and Soluble Lymphotoxin-β Peptides Lymphotoxin-β was purified by immunoaffinity-chromatography as described above. Direct N-terminal sequencing and in situ trypsin digestion followed by reverse phase HPLC resolution of the digested peptides was performed. [See, Abersold et al., "Internal Amino Acid Sequence Analysis Of Proteins Separated By One Or Two Dimensional Gel Electropherisis After In Situ Protease Digestion On Nitrocellulose," *PNAS*, 84:6970–6974 (1987)]. The resulting N-terminal and internal tryptic fragment peptides were then sequenced using conventional methods. The sequencing of the N-terminus and internal peptides, designated as T105, T87/88, T110 and T67 are shown in FIG. 13.

Two antisense 17-mer oligonucleotide probes GTYTCNGGCTCYTCYTC [SEQ ID NO:9] and GTYTCNGGTTCYTCYTC [SEQ ID NO:10], designated 1368 and 1369, respectively, were synthesized to match a portion the sequence of peptide T-87/T-88 and radiolabelled with $^{32}$P. Northern analysis showed that the probe designated 1368 hybridized strongly to a 0.9–1.1 kb mRNA band that was strongly induced in II-23.D7 cells that had been pretreated with phorbol ester as previously described.

A cDNA library in the vector pCDM8 was constructed from poly A+ mRNA isolated from II-23.D7 cells induced with PMA for 6 hours. The library was screened with the labelled oligomer designated 1368 and positive clones were isolated following washing with 3 M tetramethylammonium chloride at 50° C. Several (>16) clones containing 0.8–0.9 kb inserts were subjected to DNA sequence analysis.

Clone pCDM8/LT-β-12 contained the coding sequence of lymphotoxin-β as shown in SEQ ID NO:1. The other clones were identical except for various truncations at the 5' end. The clone 12 cDNA codes for a functional lymphotoxin-β. Using standard primer extension methods, three additional codons encoding the amino acid residues—MET GLY ALA—were identified. A termination sequence AATAAA at position 862–867 was found just prior to the 3' poly A tract indicating that the entire 3' end had been identified. The protein coding sequence encodes for 240 amino acids with a calculated unmodified molecular weight of approximately 25,390 kDa.

The 5' end of the LT-β DNA sequence identified from the clone 12 cDNA and primer extension, <u>ATG</u>GGGGCA<u>CTG</u>GGG<u>CTG</u> [SEQ ID NO:11] reveals three possible start codons (underlined). [See, e.g., M. Kozak, "An Analysis Of Vertebrate mRNA Sequences: Intimations Of Translational Control," *J. Cell. Biol.*, 115, 4:887–903 (1991).] Engineered LT-β polypeptides and DNA sequences may be derived by cleaving all or part of this 5' sequence and substituting a single start codon.

This amino acid sequence profile is typical of a type II membrane protein. Following a short (maximum 17) amino acid N-terminal "cytoplasmic" domain there is an extensive stretch of 30 hydrophobic amino acids which presumably acts as a membrane anchoring domain. No identical sequences were found within the available databases. There is one cysteine residue in the extracellular domain and two methionines within the last C-terminal 17 amino acids. This is consistent with the very limited cyanogen bromide cleavage pattern exhibited by this protein.

After the sequence of LT-β was determined, subsequent comparison revealed that LT-β is a type-II membrane protein with significant homology to TNF, LT-α and the CD40 protein. These polypeptides share four regions of sequence conservation in the extracellular domain. See FIG. 14. Such conservation regions are likely to enable those polypeptides to form complexes with each other. [See, e.g., M. Eck and S. Sprang, "The Structure Of Tumor Necrosis Factor-α At 2.6 Å Resolution, Implications For Receptor Binding," *J. Biological Chemistry*, 264, 29:17595–17605 (1989); E. Jones et al., "Structure Of Tumor Necrosis Factors," *Nature*, 338:225–228 (1989); M. Eck et al., "The Structure of Human Lymphotoxin (Tumor Necrosis Factor-β) At 1.9-Å Resolution, *J. Biological Chemistry*, 267, 4:2119–2112 (1992); J. Tavernier et al., "Conserved Residues Of Tumor Necrosis Factor And Lymphotoxin Constitute the Framework Of The Trimeric Structure," *Fed. Eur. Biochem. Soc. Lett.*, 257:2 (1989)].

Expression of Cloned LT-β

The pCDM8/LT-β clone 12* or a control plasmid, Clone 4 (pCDM8 with a non-functional LT-β cDNA insert), were introduced by electroporation into CHO dhfr⁻ cells and CHO cells stably transfected with human LT-α. After three days, cells were removed with Ca/Mg-free Hank's solution with 5 mM EDTA and stained for FACS analysis as described above using either 10 μg/ml control IgG1 or anti-LTα monoclonal antibody (Boehringer-Mannheim) followed by labelling of bound immunoglobulin with either a FITC or phycoerythrin labelled goat anti-mouse preparation.

* *E. coli* K12 bearing a plasmid pCDM8/LT-β clone 12, designated BN1289 (MC1061/P3/P33-clone-12) was deposited with ATCC on Nov. 13, 1992.

In other experiments, COS cells were electroporated with either clone 4 or clone 12 LT-β cDNA in pCDM8 in the presence or absence of an equal amount of human LT-α cDNA also in the pCDM8 vector and stained for FACS analysis after three days as above. Only CHO cells expressing LT-α displayed surface lymphotoxin upon transfection with a functional LT-β DNA, i.e., clone 12.

Clone 12 lacks an initiating ATG codon, but does possess several CTG initiating codons and hence this expression experiment shows that one or several of the 5' CTG codons must initiate translation. CTG codons are known to serve as initiating sites for translation in several eukaryotic proteins [M. Kozak, *J. Cell. Biol.*, 115, 4:887–903 (1991)]. Similar results were observed using the dual transfection system in COS cells, such that only COS cells receiving both LT-α and LT-β DNA displayed substantial surface LT-α in a FACS analysis.

Potential Uses of LT-β and LT-α and the LT-α/LT-β Complex

As noted above, there is considerable structural similarity between LT-β, LT-α, TNF and the CD40 ligand. LT-β, LT-α, TNF and the CD40 ligand are type II membrane proteins and share at least four regions of sequence conservation in the extracellular domain.

In light of this structural similarity, it is of interest that LT-α is found on the surface of activated lymphocytes in a form identical to the secreted molecule but complexed with an additional integral membrane protein presumably anchoring LT-α to the surface. We believe that this unique complex, now determined to be LT-α/LT-β, represents a more relevant form of LT-α and imparts specificity relative to TNF.

The existence of a heterometric complex of lymphokines, while unique to the immune system is reminiscent of signalling molecules in other areas, e.g., the PDGF and inhibin/activin heteromeric complexes. Delineation of the LT-α/LT-β complex poses the possibility of immunoregulatory activities unique to the complex which cannot be mimicked by the LT-α homotrimer. The complex may bind to a unique receptor or receptor chain combinations leading to a high affinity interaction and biologically relevant signalling. The hypothesis of an LT-α/LT-β interaction with a unique receptor complex could account for the relatively poor activity of the LT-α homotrimer relative to TNF in many systems, an observation which cannot be explained by studies on the two known TNF receptors. [T. Schall et al., Cell, 61:361–370 (1990); C. Smith et al., Science, 248:019 (1990)].

The tethering of soluble LT-α to the cell surface via complexation with LT-β indicates that cell-cell contact specific signalling through LT-α/LT-β may be an important aspect of immune regulation. Because the TNF and related LT-α forms are secreted we believe that LT-β may also be secreted. This may be verified in studies using anti-LT-β monoclonal antibodies. Such antibodies may also be used to determine whether LT-β homo-oligomers occur naturally.

In general, LT-α and TNF exhibit qualitatively the same spectra of activities, and LT-α and TNF are believed to interact with the same set of receptors (designated the 55 and 80 kD TNF receptors). [C. Smith et al., Science, 248:019 (1990); T. Schall et al., Cell, 61:361 (1990)]. Nonetheless, the quantitative patterns of biological potency exhibited by LT-α and TNF are dramatically different, with LT-α often being much less potent than TNF [see, e.g., Browning et al., J. Immunol., 143:1859 (1989)]. These observations are difficult to reconcile with the existing receptor binding data. It is possible that the LT-α/LT-β complex imparts unique properties on LT-α such that it now interacts with other as yet undefined receptors. In this case, a LT-α/LT-β complex and the other complexes of this invention would have unique biological properties distinguishing them from either LT-α or TNF. The LT-α/LT-β complex may be used to identify and clone such LT-α/LT-β or LT-β specific receptors. Moreover, further use of the complex may reveal novel biological activities.

Also, while a number of T cell and macrophage cell lines are known to be infectable by the HIV virus, in practice only a small number of cell lines have been useful in propagating the virus in tissue culture. For example, the H9 line, a derivative of Hut-78 originally exploited by Gallo et al. [M. Popovic et al., Science, 224:497–500 (1984)], and another human lymphocytic line, C8166, have been valuable for HIV propagation [M. Somasundaran and H. Robinson, Science, 242:1554–1557 (1988)]. It is possible that surface LT-α expression or the capacity for expression of surface LT-α makes a given cell a good target for HIV proliferation.

A role for TNF has been proposed in enhancing HIV proliferation [L. Osborn et al., Proc. Natl. Acad. Sci. USA, 86:2336 (1989); Z. Rosenberg and A. Fauci, Immunol. Today, 11:176 (1990); C. Locardi et al., J. Virology, 64:5874 (1990); G. Oli et al., Proc. Natl. Acad. Sci. USA, 87:782 (1990)]. We have found that the II-23.D7 line is infectable with the HIV strain IIIB, but upon PMA treatment the infection by the virus is dramatically increased. The Hut-78 cell line was found to constitutively express a surface LT form, and the C8166 line resembles II-23.D7 in that surface LT appears following PMA treatment. [Ware et al., J. Immunol., article in press (1992)].

Considering these results on the infectability of II-23.D7 by HIV and the relationship between infectable cell lines and surface LT expression, we propose that those lines may be good hosts for HIV infection and replication because the LT-α/LT-β complex and the other polypeptides and complexes of this invention serve a regulatory role. It has been demonstrated that the LT-α gene is induced by expression of the HIV transcriptional activator TAT [K. Sastry et al., J. Biol. Chem., 265:20091 (1990)] and, moreover, HTLV-1 infection has also been shown to induce LT-α expression [N. Paul, et al., J. Virol., 64:5412 (1990); E. Tschachler et al., in Human Retrovirology (Raven Press 1990), W. Blattner, eds., p. 105]. Thus, induction of LT-α by HIV infection and consequent LT-α/LT-β complex or other complex expression, or induction of LT-α/LT-β or other complex expression by PMA treatment in cell lines competent to make these proteins, may serve to enhance viral replication. For this reason, antibodies or specific binding proteins (e.g., soluble receptors) to the LT-α/LT-β complex or the other polypeptide complexes of this invention or to soluble forms of those complexes or to LT-β and the other polypeptides of this invention may inhibit HIV proliferation or block HIV-induced T cell death.

Parallels may be drawn between LT-α/LT-β and the CD40 receptor ligand pair where signalling from a T cell surface CD40 ligand provides "help" to the B cell via the CD40 receptor. One could therefore postulate that surface LT-α/LT-β may be a component of T cell regulation of T cells or other cells of hematopoietic lineage such as LAK or NK cells and B-cells. Moreover, this interaction may be dysfunctional in some autoimmune diseases. [See, e.g., R. Watanabe-Fukunaga, Nature, 356:314–317 (1992).]

Furthermore, a cell surface protein designated as the Fas antigen has been shown to have considerable structural homology with a number of cell-surface receptors including TNF, NGF and the CD40 protein. The Fas antigen has been implicated in mediating apoptosis, a process also referred to as programmed cell death [R. Watanabe-Fukunaga, Nature, 356:314–317 (1992); N. Itoh et al., Cell, 66:233–243 (1991)]. A strain of mice that demonstrates defects in the Fas antigen develop a systemic lupus erythematosus-like autoimmune disease. This suggests that the structurally similar LT-β or LT-α/LT-β complexes may also play a role in mediating systemic lupus erthyematosus and, therefore, intervention in this pathway may be clinically useful in treating various autoimmune diseases. Alternatively, LT-β or an LT-α/LT-β complex may be involved in inducing programmed cell death through a cell-cell contact dependent mechanism. The emergence of this family of TNF related ligands to complement the already extensive family of TNF/NGF type receptors suggests the existence of an additional array of important regulatory elements within the immune system.

LT-β or a LT-β/LT-α complex may similarly play a role in suppressing the immune system and may be potentially useful in treating allergy and inducing tolerance.

The location of the TNF/LT locus in the MHC region of the genome has led workers to examine linkage to various autoimmune disease, especially insulin-dependent diabetes melitis. [See, e.g., F. Pociot et al., "A Tumor Necrosis Factor Beta Gene Polymorphism In Relation To Monokine Secretion And Insulin-Dependent Diabetes Mellitus," Scand. J. Immunol., 33:37–49 (1991); K. Badenhoop et al., "TNF-α Gene Polymorphisms In type 1 (Insulin-Dependent) Diabetes Mellitus," Diabetologia, 32:445–448 (1989).] Because we found that the LT-β gene is located next to the TNF/LT locus, it is possible that the LT-β gene or its receptor may be involved in this autoimmune condition. Hence, LT-β or its receptor or antibodies to LT-β may comprise a replacement therapy in this form of diabetes.

As discussed above, the LT-β polypeptide, and the polypeptide complexes of this invention, are expected to have a number of potential uses including anti-tumor, T cell activating, or T cell suppressing applications, application involving the treatment of systemic lupus erythematosus, as well as uses in anti-inflammatory compositions and methods. DNA sequences coding for LT-β polypeptides, recombinant DNA molecules including such DNA sequences, and unicellular hosts and animal or human cells in culture transfected with such recombinant DNA molecules may then be employed to produce large amounts of the polypeptides of this invention, substantially free from other human proteins, for use in the compositions and therapies noted above.

Lymphocytes expressing on their surfaces the polypeptide complexes of this invention, and preferably an LT-α/LT-β complex, represent a subset of lymphocytes that may have enhanced abilities to kill tumor cells. As such, this subset would be useful in LAK (lymphokine-activated killer) cell or TIL (Tumor Infiltrating Lymphocyte) cell therapies. [H. Thomas, K. Sikora, "Biological Approaches to Cancer Therapy," *Jour. Int. Med. Res.*, 17:191 (1989)]. TIL immunotherapy may be improved by gene transfer techniques. Recombinant genes for LT-β and related polypeptides based thereon will be useful therapeutically, for example in TIL therapy, where a LT-β gene, either with or without an LT-α gene, is introduced into T cells isolated from a tumor and introduced to the patient. More preferably, the cells are taken from the patient, transfected with a DNA sequence encoding on expression a polypeptide of this invention, before or after that transfection incubated with a lymphokine, preferably IL-2, and returned to the patient. The transfected T cells (now expressing LT-β and also consequently complexing LT-α) home in on the tumors from which they were removed, where the tumorcidal action of LT-α is delivered directly to the tumors. Likewise, it is contemplated that a LT-β gene introduced into LAK cells would increase the number of surface complexes on the cells and enhance their activity. Alternatively, introduction of the LT-β gene into a patient's tumor cells may be useful in creating a tumor vaccine in which the LT-β modified tumor would trigger an enhanced immune response to the tumor itself. [See, e.g., W. F. Anderson, *Science*, 256:808–813 (1992)].

Antibodies or antibody derivatives to the polypeptides and polypeptide complexes of this invention are also useful in conventional immunological methods, e.g., panning or flow cytofluorometric sorting, to enrich for this cell population. [L. J. Wysocki and V. L. Sato, "Panning for Lymphocytes: A method for Cell Selection," *PNAS* 75:2844 (1978)].

It is also contemplated that the polypeptides and polypeptide complexes of this invention, or fragments or derivatives thereof, will be useful in cell regulatory or therapeutic applications similar to those in which lymphotoxin-α and tumor necrosis factors are used.

The compositions of this invention will be administered at an effective dose to treat the particular clinical condition addressed. Determination of the particular dose for a given application is well within the skill of the art taking into consideration, for example, the condition and weight of the patient, the extent of desired treatment and the tolerance of the patient for the treatment. Administration of the complexes and polypeptides of this invention, or perhaps peptides derived or synthesized therefrom or using their amino acid sequences, including isolated and purified forms of the polypeptides, or their salts or pharmaceutically acceptable derivatives thereof, may be via any of the conventionally accepted modes of administration of agents which exhibit anti-tumor, T cell-activating, T cell-suppressing or anti-inflammatory activity.

The compositions used in these therapies may also be in a variety of forms. These include, for example, solid, semi-solid and liquid dosage forms, such as tablets, pills, powders, liquid solutions or suspensions, suppositories, injectable and infusible solutions, and genetic therapy. The preferred form depends on the intended mode of administration and therapeutic application. Modes of administration may include oral, parenteral, subcutaneous, intravenous, intralesional or topical administration. The compositions also will preferably include conventional pharmaceutically acceptable carriers and may include other medicinal agents, carriers, genetic carriers, adjuvants, excipients, etc., e.g., human serum albumin or plasma preparations. Preferably, the compositions are in the form of a unit dose and will usually be administered one or more times a day.

The following are examples which illustrate the LT-β and the LT-α/LT-β complex of this invention and the methods used to characterize them. These examples should not be construed as limiting: the examples are included for purposes of illustration and the present invention is limited only by the claims.

EXAMPLES

We used the following experimental procedures in the examples:

Antisera

Recombinant human LT-α(rLT-α) was expressed and secreted by a stably transfected chinese hamster ovary (CHO) cell line into serum-free conditioned media. We purified the secreted rLT-α from the serum-free conditioned media by a series of Sepharose S, lentil lectin-sepharose and FPLC Mono Q column chromatography steps. The properties of the CHO cell-derived rLT-α preparation have been described. [J. Browning et al., *J. Immunol.*, 143:1859 (1989)]. We immunized two rabbits (4 and 5) by a lymph node procedure [M. Sigel et al., "Production Of Antibodies By Inoculation Into Lymph Nodes," *Met. Enz.*, 93:3 (1983)] with 25 µg of native rLT-α in complete Freund's adjuvant. A third rabbit (6) was immunized via the same route with 25 µg of denatured rLT-α in complete Freund's adjuvant. We prepared denatured rLT-α by SDS-PAGE followed by electroelution into 0.1% SDS-carbonate buffer.

Using the above methods, three anti-rLT-α antisera were generated, two directed against native rLT-α and a third against SDS-denatured rLT-α. The antisera raised by immunization with native protein (rabbits 4 and 5) could neutralize a 50 unit/ml solution at a dilution of 1:2000–5000. The serum raised against denatured rLT-α (rabbit 6) lacked neutralizing titer, but was weakly reactive with rLT-α on a Western blot. None of the antisera could neutralize r-human TNF nor could they recognize r-human TNF bound to an ELISA plate except for a very weak titer in the antiserum from rabbit 6. Only antiserum from rabbit 6 was capable of recognizing rLT in a western analysis.

We immunized a fourth rabbit with recombinant human TNF. We prepared the polyclonal anti-rTNF rabbit serum via a classical immunization scheme using recombinant human TNF (*E. coli* derived [D. Weir et al., *Handbook Of Experimental Immunology In Four Volumes*, Chapter 8 "Immunization Of Experimental Animals"]) in complete Freund's adjuvant followed by a boost in incomplete Freund's adjuvant. The serum raised against rTNF by immunization had a good neutralizing titer. A neutralizing monoclonal antibody to TNF has been described [Liang et al., "Production And Characterization Of Monoclonal Antibodies Against Recombinant Human Tumor Necrosis Factor/Cachectin," *Biochem. Biophys. Res. Comm.*, 137:847 (1986)]. Pre-immunization serum was collected from all animals for use as controls.

Cell Growth and T Cell Activation

All cells were obtained from the American Type Culture Collection (ATCC), except for the LT-α transfected Chinese hamster ovary (CHO) line that was described previously [Browning, *J. Immunol.*, 143, pp. 1859–1867 (1989)].

Cells were grown in RPMI 1640 supplemented with 1% glutamine, 10 mM HEPES buffer, pH 7.5, penicillin/streptomycin and 10% fetal bovine serum (Hyclone-defined) (designated "complete RPMI"), except for the transfected CHO cells which were grown in Dulbecco's modified Eagle's medium supplemented as above. The human T cell hybridoma, II-23, was a result of a fusion of the human CEM tumor line with activated peripheral T lymphocytes and was further subcloned (II-23.D7) [C. Ware et al., "Human T Cell Hybridomas Producing Cytotoxic Lymphokines: Induction of Lymphotoxin Release And Killer Cell Activity By Anti-CD3 Monoclonal Antibody Or Lectins And Phorbol Ester," *Lymph. Res.*, 5, 313 (1986)]. Human peripheral blood lymphocytes (PBL) were drawn into heparinized glass tubes, isolated by Ficoll-Hypaque centrifugation, washed and resuspended in complete RPMI medium. We treated PBL at $2\times10^6$ cells/ml with a 1:500 dilution of OKT3-conditioned medium (~2 ng/ml final) in the presence of 1 μg/ml indomethacin and, in some experiments, with 10 ng/ml rIL-2 (Biogen, Inc., Cambridge, Mass.)). Human CTL-clones were generated as described [L. Green et al., "Cytotoxic Lymphokines Produced By Cloned Human Cytotoxic T Lymphocytes," *J. Immunol.*, 135:4034 (1985)] and activated either with irradiated stimulator cells (antigen) or a combination of anti-CD2 monoclonal antibodies ($T11_2+T11_3$) provided by E. Reinherz.

Flow Cytometry

We resuspended cells in RPMI 1640 medium with 10% fetal bovine serum (FBS), 0.1% sodium azide and 0.1 mg/ml human IgG at 0° C. Following preincubation with the human IgG, we added additional media containing the desired antisera. Typically the cells were incubated with a final dilution of the anti-rLT-α and anti-rTNF sera of 1:200 for 60–90 min. We washed cells twice with Dulbecco's phosphate buffered saline (PBS) and then incubated them with a 1:500 dilution of fluorescein-labeled goat anti-rabbit IgG (Cappel Durham, N.C.) in the above medium for a minimum of 60 min. Cells were then washed once and either analyzed directly or, in some cases, analyzed following fixation for 10 min. at 0° C. with 0.5% paraformaldehyde. We performed two color analyses as above, except that we added phycoerythrin labeled leu-4, leu-2, leu-M3 or leu-16 or leu-19 (Becton-Dickinson, Mountain View, Calif.) at the second antibody stage. The comparison of surface-bound LT-α with IL-2 receptor levels was done with separate single color analyses with fluorescein-labeled anti-IL-2 receptor (CD25) antibody (Becton-Dickinson, Mountain View, Calif.). Analyses were performed with a FACStar instrument (Becton-Dickinson).

Adsorption of Neutralizing Anti-rLT-α Antibodies by Activated II-23.D7 Cells

We stimulated II-23.D7 and U937 premonocytic cells at $1\times10^6$ cells/ml for 8 hours with 10 ng/ml of PMA in complete RPMI medium. We washed the cells ($1\times10^8$) three times in medium and aspirated the supernatant to obtain a dry pellet. The cells were then resuspended in 1 ml of medium containing a 1:1000 dilution of anti-rLT-α serum (from rabbit 4) and incubated on ice for 1.5 hours with mixing. Cells were cleared from the antiserum by centrifugation. We mixed the absorbed antiserum (both pre-and post-immune) with an equal volume (50 μl) of medium containing 15 U/ml of rLT-α and incubated for 20 minutes at room temperature. The mixtures were diluted serially into medium and added to L929 cells (in 0.1 ml) and incubated a further 24 hours. We assessed cell viability by the MTT assay as described [L. Green et al., "Rapid Colorimetric Assay For Cell Viability: Application To The Quantitation of Cytotoxic And Growth Inhibitory Lymphokines" *Jour. Immunol. Meth.*, 70:257–268 (1984)].

$^{35}$S-Methionine or $^{35}$S-Cysteine Metabolic Labelling of T Cells

We transferred cells into either cysteine-free or methionine-free RPMI 1640 supplemented with penicillin/streptomycin, glutamine, 10 mM HEPES pH 7.5, 10% v/v dialyzed FBS and 2% v/v conventional RPMI (cold carrier addition). We adjusted the cell concentration to $2-3\times10^5$ cells/ml and added $^{35}$S-methionine or $^{35}$S-cysteine to the appropriate medium to a level of 100–200 μCi/ml. In the case of freshly activated PBL, the supernatants were gently removed, and the cells were centrifuged, resuspended in labelling medium and added back to the original adherent population. Following a 12–18 hour labelling period, we washed and lysed the cells as described below. With the PBL, cells were removed by pipetting and the adherent population partially removed by treatment with 5 mM EDTA in PBS.

Immunoprecipitations

To 0.2–0.5 ml of labeled cell lysate we added 2–4 μl of rabbit serum. The sample was left for 1–2 hours at 4° C. We then added a 60 μl aliquot of a 60–75% suspension of washed Protein A sepharose (Pharmacia, Piscataway, N.J.) and rocked the sample for 6–18 hours at 4° C. We washed the Protein A sepharose pellets 3 times with 1% NP-40 in calcium/magnesium free PBS and resuspended them in 50 μl of Laemmli SDS loading buffer. Typically a single lysate sample was cycled through sequential immunoprecipitations with preimmune anti-rLT-α serum, anti-rTNF antiserum and finally post immune anti-rLT-α antiserum. In one set of experiments, we added 5 mM $CaCl_2$ and $MnCl_2$ to the lysate and the lysate was rocked overnight with 75 μl of 75% suspension of washed lentil lectin-sepharose. The sepharose was washed twice with NP-40/PBS and then eluted with 3 consecutive additions of 75 μl of 1% NP-40/PBS with 0.25 M α-methyl mannoside. We subjected the pooled washes to the immunoprecipitation protocol.

Rabbit Anti-rLT Affinity Column

We purified the immunoglobulin fraction from the anti-rLT serum (from rabbit 4) using Protein A sepharose with acid pH elution. The eluted IgG-containing fractions were dialyzed against PBS and concentrated by amicon filtration. The anti-rLT-α-IgG solution (15 ml of 6 mg/ml) was coupled to 8 ml of Affi-gel 10 resin (Biorad, Richmond, Calif.) as per instructions. We prepared an identical affinity column using nonspecific rabbit IgG (Cappel, Durham, N.C.). Both columns were washed with PBS, 1 M acetate pH 3.0 with 1% NP-40 and finally with lysis buffer lacking protease inhibitors.

Initial Purification of LT-β and LT-α

We grew II-23.D7 cells (15 l) to a density of $5\times10^5$ cells/ml and added phorbol myristic acetate (PMA) to give a final concentration of 25 ng/ml. After 24 hours, we harvested the cells and washed them into cold serum-free RPMI medium. To the chilled cell pellet containing $7\times10^9$ cells we added 100 ml of ice-cold lysis buffer (50 mM HEPES pH 7.5, 1% v/v NP-40, 2 mM EDTA, 0.15 M NaCl and 0.1% sodium azide) to which 5 mM benzamidine, 1 mM phenyl methyl sulfonyl chloride (PMSF) and 0.25 mM N-ethyl maleimide (NEM), 10 ig/ml soybean trypsin inhibitor, 0.7 µg/ml pepstatin and 10 µg/ml aprotinin had been freshly added. We gently homogenized the cells in a dounce homogenizer and centrifuged the lysate at 10,000×g for 10 minutes. We centrifuged the supernatant at 60,000×g for 90 minutes and collected the supernatant.

To the supernatant from the high speed centrifugation we added 5 mM $CaCl_2$ and 5 mM $MnCl_2$. The supernatant was then loaded onto a 20 ml lentil-lectin sepharose column (Pharmacia, Piscataway, N.J.) equilibrated in lysis buffer plus $CaCl_2$ and $MnCl_2$. We washed the column with lysis buffer (with $CaCl_2$ and $MnCl_2$) and then eluted the column with lysis buffer containing 0.25 M α-methyl mannoside.

We pooled the lentil lectin eluate fractions to give a volume of 50 ml and loaded them directly onto a 2 ml rabbit nonspecific IgG sepharose affinity column. We connected this column directly to a 2 ml rabbit anti-rLT-α sepharose affinity column. We washed both columns with the same lysis buffer with EDTA, followed by lysis buffer wherein the 1% NP-40 had been replaced with 1% w/v MEGA-8 (Octanoyl-N-methyl glucamide, Boehringer-Mannheim, Indianapolis, Ind.).

We eluted the washed columns individually with 1% MEGA-8, 50 mM glycine pH 2.5, 0.05 M NaCl, 5 mM benzamidine, and 2 mM EDTA. We pooled the first 20 ml following the pH shift, lyophilized the pool and resuspended it in 1 ml of water with 0.05% SDS, and dialyzed it against 10 mM HEPES pH 7.5, 0.05% SDS and 0.1% MEGA-8. We dried the dialyzed fractions on a speed-vac and resuspended them in 0.15 ml of water. We mixed aliquots with Laemmli loading buffer and electrophoresed them on SDS-PAGE. The LT-β and LT-α proteins were visualized by silver staining.

Iodination of II-23.D7 Cell Surface

Either control or PMA-induced II-23.D7 cells were washed extensively in calcium/magnesium-free PBS, treated with 1 mM PMSF and 0.25 mM NEM and then washed twice. To a 12×75 mm glass tube that was coated with 50 µg of iodogen (Pierce) we added 0.3 ml of cells ($1\times10^7$ total) and 1–2 mCi of $^{125}$sodium iodide. Cells were left with periodic swirling for 25 minutes at room temperature, washed 3 times in PBS with 10% FBS and resuspended in lysis buffer as described above. We then removed the nuclei with a 2 minute centrifugation in an Eppendorf centrifuge. We then centrifuged the supernatant an additional 15 minutes. The cleared supernatant was subjected to the immunoprecipitation protocol.

1-Dimensional CNBr Peptide Mapping

We electrophoresed samples on a 12% acrylamide SDS-PAGE Laemmli system gel for a short distance and excised the appropriate gel sections. We soaked the gel slices for 1 hour in 1.0 ml of 0.1 N HCl, 0.2% 2-mercaptoethanol with 15 µl of 700 mg/ml fresh CNBr in 90% formic acid. The slices were then removed and washed for 5 minutes with 0.1 M Tris-Cl pH 8.0, 5 min with 25 mM Tris-Cl pH 8.0 and finally 10 min with 1× Laemmli SDS-PAGE loading buffer. We loaded the slices onto a 15% SDS-PAGE Laemmli gel with a 12% acrylamide stacking gel. We visualized the peptide bands by silver staining or autoradiography of the dried gel.

Reimmunoprecipitation

Reimmunoprecipitation of SDS-PAGE-separated antigens was carried out by excising labeled bands from gels, rehydrating them for 10 minutes in TBS, 0.2% SDS, and then dicing the gel slices into small pieces. The proteins were eluted by incubation in 1 ml TBS, 0.2% SDS for 8 hours at room temperature, with rotation. After elution the gel pieces were removed by centrifugation, and NP-40 was added to the supernatant to a final concentration of 2%. The eluted proteins were then immunoprecipitated as above, and reanalyzed by SDS-PAGE.

Isoelectric Focusing (IEF)

Two-dimensional IEF was performed essentially as described by P. H. O'Farrell [*J. Biol. Chem.*, 250:4007–4021 (1975)]. $^{125}$I-labeled antigens were immunoprecipitated from II-23.D7 cell extracts, and the immunoprecipitated proteins were eluted by heating at 100° C. for 5 minutes in 100 µl O'Farrell sample buffer containing 9.5 M urea. The eluted proteins were then focused (first dimension) on 14 cm×3 mm tube gels possessing a 2% final concentration of ampholines (range pH 3–10, Sigma) at room temperature for 16 hours at a constant voltage (400 V). The second dimension was 12% SDS-PAGE.

For IEF under native (non-denaturing) conditions, 125I-labeled cell extracts were focused directly on tube gels identical to those above except for the presence of urea. The labeled extract (200 µl volume) was centrifuged at 100,000×g (30 psi, airfuge) for 10 minutes prior to loading onto the tube gel. The focusing was performed at 4° C. under the same conditions as described above. The tube gel was then removed and sliced into 1 cm sections, and the proteins were eluted by incubating each slice in 1 ml TBS, 2% NP-40, 2 mM PMSF for 8 hours at room temperature, with rotation. The supernatants containing the eluted proteins were then immunoprecipitated and analyzed by SDS-PAGE. The pH gradients for both the denatured and native tube gels were determined by measuring the pH's of individual slices from gels run in parallel.

T Cell Proliferation Assays

We isolated and resuspended PBL in complete RPMI as described above except for the substitution of fetal bovine serum with 10% human autologous serum, 1 µg/ml indomethacin and 50 U/ml polymyxin B. In the MLR experiments, autologous serum was the responder's serum. We irradiated stimulator cells from a different donor with 3000 rads. We preheated rabbit sera for 1 hour at 56° C., and diluted and sterile filtered the sera prior to use in proliferation assays. Cells ($1\times10^5$ total) in 0.2 ml in a round bottom 96-well plate were treated with either 5 µg/ml phytohemagglutinin, 1–2 ng/ml OKT3 or $1.5–2\times10^5$ irradiated stimulator cells in the presence or absence of various antisera or cytokines. After 3 days (PHA or OKT3 activation) or 5 days (MLR), cells were pulsed with $^3$H-thymidine, harvested and counted.

Further Purification of LT-α and LT-β

We grew II-23.D7 cells in RPMI medium with 10% fetal bovine serum and we harvested the cells from 50 1 RPMI medium and resuspended them in medium at a concentration of $4\times10^6$ cells/ml and we added 50 ng/ml phorbol myristoyl acetate (PMA). After activation for 6 hours we harvested the cells by centrifugation and washed them with Dulbecco's phosphate buffered saline. We suspended the final cell pellet of $4\times10^{10}$ cells in 200 ml of cold lysis buffer (50 mM HEPES buffer, pH 7.0; 0.1 M NaCl, 10 mM EDTA, 5 mM benzamidine, 10 µg/ml each of soybean trypsin inhibitor, aprotinin, chymostatin, leupeptin, antipain, 1 µg/ml pepstatin and 1 mM phenylmethyl sulfonyl fluoride) and passed the pellet once through a nitrogen cavitator. We centrifuged the lysed the cells at 40,000 rpm for 60 minutes in a 50.2 Ti rotor and discarded the supernatant. We extracted the pellet overnight in 120 ml of lysis buffer with 1% w/v Nonidet P40 detergent and then centrifuged it as above.

We added the supernatant containing the detergent solubilized membrane proteins to 2 ml of affinity resin composed of monoclonal anti-lymphotoxin (anti-tumor necrosis factor-β from Boehringer Mannheim) coupled to Affi-gel 10 (BioRad) and rocked the suspension overnight. We collected the resin into a small column and washed it with 50 mM HEPES, pH 7.0 with 1% Nonidet P40, and then with the same buffer with 1% w/v MEGA-8 (Boehringer Mannheim). We eluted the bound proteins with 1% MEGA-8 in 50 mM glycine buffer pH 2.5 and the fractions immediately neutralized with Tris base. We determined the presence of p33 and LT in the fractions by SDS-PAGE analysis and silver staining. We pooled factions containing these proteins and added SDS to a final concentration of 0.1% w/v and we dialyzed the pool against 0.1× Laemmli sample buffer (multiple changes to remove the MEGA-8 detergent). We lyophilized the dialyzed solution to dryness and resuspended it in 1/10th the original volume of water. We ran the sample on an SDS-PAGE gel, blotted onto a ProBlot membrane (Applied Biosystems) and stained with coomassie blue dye.

This scheme allows one to purify LT-β to a band on a blot. It should be possible for anyone skilled in the art to separate the proteins eluted from the affinity resin by ion exchange chromatography. For example, the complex can be dissociated with urea and the LT-α and LT-β proteins can be separated by, e.g., MONO Q FPLC (Pharmacia) anion exchange chromatography in Tris-Cl buffer pH 8.0 with 1% nonionic detergent (e.g., MEGA-8, Boehringer-Mannheim) and urea, using a salt gradient elution. This chromatographic technique separates on the basis of differing charges on the proteins. The two proteins are separable in an isoelectric focusing experiment (see, supra) on the basis of charge differences, wherein urea is used to dissociate the LT-α/LT-β complex. Such a combination of affinity chromatography, dissociation in urea/nonionic detergent and ion exchange chromatography allows purification of soluble LT-β or the LT-α/LT-β complex.

Peptide Sequencing Assays

We excised the LT-β and LT-α bands from the Problot and loaded them into a protein sequencer. We obtained N-terminal sequence information by Edman degradation with a model 470A Applied Biosystems sequencer coupled to a 120A PTH amino acid analyzer. LT-β was purified by immunoaffinity-chromatography as described above and tryptic fragment sequence was obtained. [See Abersold et al., "Internal Amino Acid Sequence Analysis Of Proteins Separated By One Or Two-Dimensional Gel Electrophoresis After In Situ, Protease Digestion On Nitrocellulose," PNAS:84:6970–6974 (1987)]. That is, protein on the blot was digested with trypsin in situ followed by reverse phase HPLC resolution of the digested peptides. The resulting N-terminal and internal tryptic fragment peptides were then sequenced by Edman degradation. The sequencing of the N-terminal and internal peptides designated as T105, T87/88, T100 and T67 are shown in FIG. 13.

Construction of Oligonucleotide Probes

From the sequence of T87/88 the following antisense probes were designed:

```
1368      GTYTCNGGCTCYTCYTC     [SEQ ID NO:9]

1369      GTYTCNGGTTCYTCYTC     [SEQ ID NO:10]
``` and synthesized by standard methods. [See, e.g., J. Sambrook et al., Molecular Cloning, A Laboratory Manual, 2ed. (1989)].

Preparation of an Induced II-23 cDNA Library

We prepared a cDNA sublibrary as follows:

We stimulated II-23.D7 cells for six hours with 50 ng/ml PMA to ensure the presence of LT-β mRNA. We isolated the mRNA from these cells and reverse-transcribed it into cDNA using techniques well known to the art. [B. Seed and A. Aruffo, "Molecular Cloning Of The CD2 Antigen, The T-Cell Erythrocyte Receptor, By A Rapid Immunoselection Procedure," PNAS,84:3365–3369 (1987)]. Using standard procedures, we ligated double stranded cDNA to a NotI-BstXI linker/adaptor having the following sequence:

```
5'  GCG GCC GCT TTA GAG CAC A 3'      [SEQ ID NO:12]

3'  CGC CGG CGA AAT CTC 5'
```

We then size-selected the cDNA on a 4.2 ml 5–20% potassium acetate gradient, 2 mM EDTA, 1 μg/ml ethidium bromide, in a Beckman® SW60 Rotor for 3 hours at 50,000 rpm at 22° C. according to standard methods. We pooled the cDNA fragments of greater than 500 base pairs. Then we prepared the vector, pCDM8 (a gift from Brian Seed (Massachusetts General Hospital). We digested this plasmid with BstXI. To remove the 400 base pair stuffer fragment we centrifuged the mixture on a potassium acetate gradient, as above, and isolated the large fragment. We further purified this fragment by agarose gel electrophoresis, and then ligated the cDNA to the vector. In this way, we created recombinant DNA molecules containing DNA sequences for mRNA expressed in induced II-23.D7 cells. We used these plasmids to transform E. coli MC1061 P3. The result was a collection of over 1×10$^6$ recombinant clones comprising a cDNA library for PMA induced II-23.D7 mRNA.

Screening and DNA Sequencing of Clones

The pCDM8 II-23.D7 library was screened with $^{32}$P labelled oligomer 1368 and positive clones were isolated following washing with 3M tetramethylammonium chloride at 50° C. [J. Sambrook et al., Molecular Cloning, A Laboratory Manual, (1989); Jacobs et al., "The Thermal Stability Of Oligonucleotide Duplexes In Sequence Independent In Tetraalkylammonium Salt Solutions: Application To Identifying Recombinant DNA Clones", Nucleic Acids Research, 16:10:4637–4649 (1988)]. Several clones containing 0.9 kb inserts were subject to dideoxynucleotide DNA sequence analysis [Id.].

Expression of LT-β cDNA

The pCDM8/LT-β clone 12 or a control plasmid, clone 4 (pCDM8 with an irrelevant cDNA insert), was introduced by electroporation into CHO dhfr⁻ and a CHO cell stably transfected with human LT-α. After three days, cells were removed with Ca/Mg-free Hank's solution with 5 mM EDTA and stained for FACS analysis as described above using either 10 μg/ml control IgG$_1$ or anti-LT monoclonal antibody (Boehringer-Mannheim) followed by labelling of bound immunoglobulin with either a FITC or phycoerythrin labelled goat anti-mouse preparation. In other experiments, COS cells were electroporated with either clone 4 or clone 12 LT-β cDNA in pCDM8 in the presence or absence of an equal amount of human LT-α cDNA also in the pCDM8 vector and stained for FACS analysis after three days as above.

Northern Analysis of LT-β Expression

Poly A+ RNA was isolated from either II-23.D7 cells or peripheral blood mononuclear cells (PMBC) using the Fast-Track™ system provided by Invitrogen. Northern blots were prepared using 2 μg/lane of RNA and electrophoresis on a formamide gel essentially as described in J. Sambrook et al.,

*Molecular Cloning, A Laboratory Manual,* (1989), followed by transfer onto Gene Screen nylon membrane and UV crosslinking. Blots were probed with random primed BstEII/Xmn-I fragment of the LT-β cDNA which had been gel purified, or a fragment of human LT-α or actin. II-23.D7 cells were induced with 50 ng/ml PMA for varying times and both LT-α and LT-β expression was found to be induced. PBMC were either cultured in RPMI medium alone or in the presence of 1000 units/ml of IL-2 or with OKT3 to activate the T-cells.

Determination of the 5' End of LT-β

The 5' mRNA sequence was determined by primer extension analysis. [B. Wallner et al., Nature 320:77–81 (1986).] Primer extension using an oligonucleotide primer (probe 360-121 5'GACAGTGATAGGCACCGCCAGCAACAA-3') [SEQ ID NO:13] yielded a roughly 128–130 bp product that upon sequencing using Maxam and Gilbert methodology [A. Maxam and W. Gilbert, "Sequencing End-Labeled DNA With Base-Specific Chemical Cleavages," *Methods In Enzymology,* 65:499 (1988)] showed the transcriptional start site to be 7–9 bp upstream of the methionine ATG. The expression exhibited by clone 12 in transient experiments indicates that one or both of the Leu-4 or Leu-6 start site is functional. To verify the 5' mRNA sequence, a cosmid clone, 031A [Spies et al., Science 243:214 (1989)], was digested with several restriction enzymes, electrophoresed, blotted and probed with a BST E2/Xmn-1 fragment of the LT-β cDNA. The cosmid contained the LT-β gene within a 6 kb EcoR1 fragment which was subcloned into a pUC derivative called pNN 109 which contained a kanamycin resistance gene. Dideoxynucleic acid sequencing gave the entire genomic sequence.

Example 1
T Cells Express LT-Related Epitopes on their Surfaces

Under the conditions described above, we activated human peripheral mononuclear cells (PMN) with OKT3 monoclonal antibody and, after two days in culture, we analyzed them for expression of LT-α/LT-β complex related forms using flow cytofluorometric analysis. In one experiment, the results of which are shown in FIG. 1, we cultured fresh PBL for 3 days with OKT3 and IL-2 and stained them with a 1:200 dilution of antisera to native rLT-α ("LT-4" and "LT-5" panels on FIG. 1, from rabbits 4 and 5 respectively), denatured rLT-α ("LT-6" panels on FIG. 1, from rabbit 6) and native rTNF ("TNF" panel on FIG. 1, from rabbit 7). We stained cells with postimmune serum (solid lines on FIG. 1 panels) or with preimmune serum from each animal (dotted lines on FIG. 1 panels). FIG. 1 shows that only anti-rLT-α sera from rabbits 4 and 5 recognized epitopes on the activated peripheral T cells.

Figure 2A:
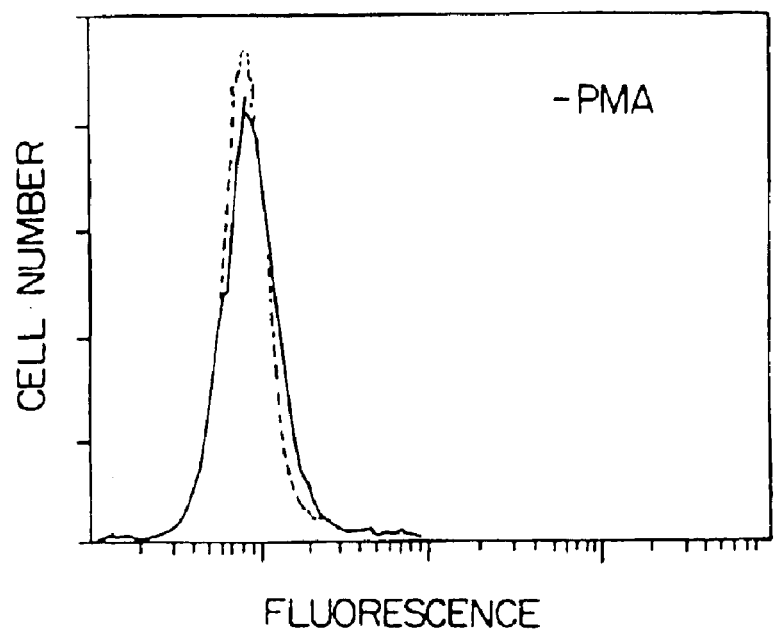
FIG. 2 depicts flow cytofluorometric analysis of a human T cell hybridoma, II-23.D7, showing the presence (following PMA treatment) of a LT-α-related epitope on the cell surface.
Figure 2B:
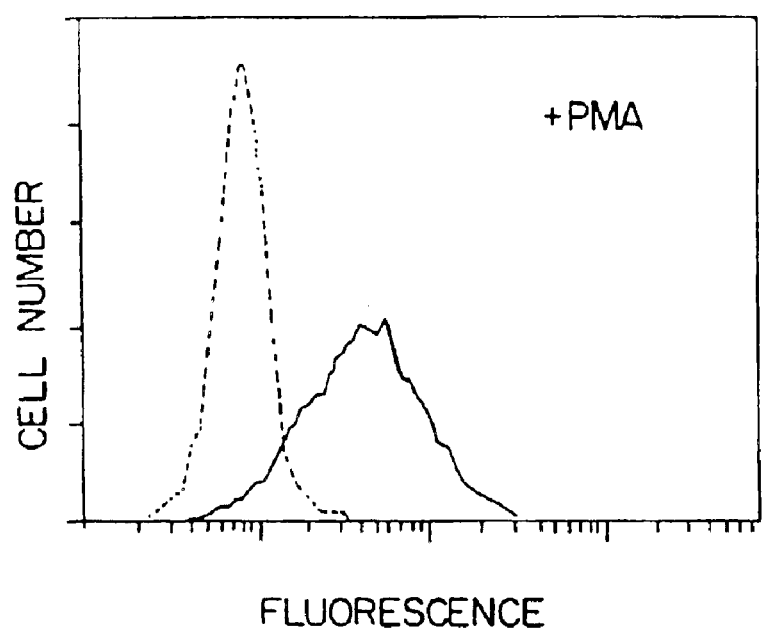

In the experiment shown in FIG. 2, we treated II-23.D7 cells with or without 10 ng/ml PMA for 15 hours and stained them as described in the FIG. 1 experiment, with rabbit 4 anti-rLT-α postimmune serum (solid line on FIG. 2 panels) or with rabbit 4 preimmune serum (dotted line on FIG. 2 panels). As shown in FIG. 2, we found that the T cell hybridoma II-23.D7, which synthesizes LT-α upon phorbol ester (PMA) stimulation, expressed surface LT-related epitopes upon PMA activation.

Figure 3:
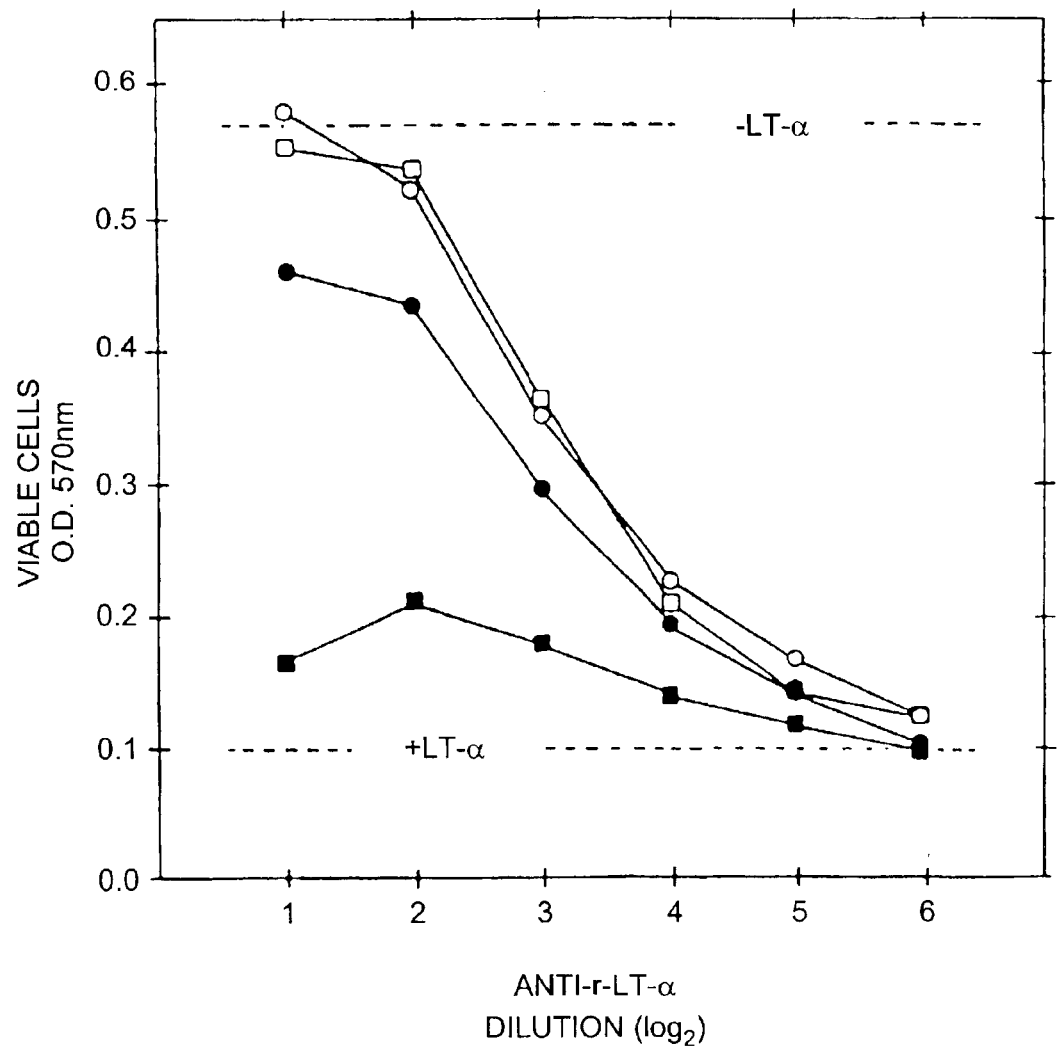
FIG. 3 depicts the ability of PMA activated II-23.D7 cells to bind anti-rLT-α antibodies. Samples of anti-rLT-α antisera were incubated with PMA-treated U937 (non-LT-producing) cells, (—O—), PMA-activated II-23.D7 hybridoma cells ($10^8$, - -; $10^7$, - -), and no cells (control, - -). Serial dilutions of the cell-free antisera after incubation were added to rLT-α and used in a cytotoxicity assay against L929 (LT-α-sensitive) cells. The plots indicate that rLT-α neutralizing antibodies were removed from the antisera by the activated II-23.D7 cells.

To establish that the LT-α-related epitopes on T cells were related to LT and not to some contaminant in the CHO-cell derived recombinant LT-α preparation, we treated a 1:1000 dilution of antiserum from rabbit 4 with PMA-activated, washed II-23.D7 or U937 cells. In the experiment shown in FIG. 3, we treated a 1 ml sample of anti-rLT-α sera (1:1000 anti-LT-4) with either no cells (- -), 1×10$^8$ U937 cells (—O—), 1×10$^8$ (- -) PMA-activated II-23.D7 cells or 1×10$^7$ (- -) PMA-activated II-23.D7 cells. We added dilutions of absorbed antisera to a limiting amount of rLT-α in a L929 cytotoxicity assay such that a 1:4000 final dilution was present in the first well. This assay measures the ability of LT-α to kill a mouse fibroblast cell line, L929, within a 24 hour period [L. Green, J. L. Reade, C. F. Ware, "Rapid Colorimetric Assay for Cell Viability: Application to the Quantitation of Cytotoxic and Growth Inhibitory Lymphokines," *J. Immunol. Methods,* 70:257 (1984)]. After 24 hours, we assessed cell viability using a MTT readout. Plotted on FIG. 3 is optical density (which is proportional to cell viability) vs. the dilution of absorbed antisera. Data represent the average of duplicate wells and duplicates generally were within the range defined by the symbol. As shown in FIG. 3, analysis of the neutralizing titer of the absorbed antisera in the standard L929 cytotoxicity assay demonstrated that the activated II-23.D7 cells removed the LT-α neutralizing antibodies, whereas U937 cells were ineffective. These data indicate that the antigenic structures on the membrane surface are actually related to LT-α.

We subjected the hybridoma II-23.D7 to a number of further treatments to examine a number of trivial explanations for the apparent existence of LT-α related epitopes on T cell surfaces. First we ruled out the possibility that LT-α:antibody complexes in the antisera could bind to TNF/LT-α receptors on the hybridoma. Both TNF and LT-α have trimeric structures which could allow for the presence of antibody binding epitopes within the complex. However, prior saturation of the cellular TNF receptors with soluble TNF or LT-α had no effect on the surface staining. Such saturation should have prevented such an immune complex from binding to such a receptor.

A pH 3 lactic acid treatment, which can release bound TNF from its receptor, had no effect on the signal, suggesting that the LT-α is not receptor bound. However, experiments utilizing $^{125}$I-LT-α binding to II-23.D7 cells indicated that receptor bound LT-α was more difficult to remove from its receptor at acidic pH's than TNF.

Mild trypsinization of the cells prior to staining led to a loss of the signal, indicating that the epitope is a protein. To determine whether surface-associated LT-α was phosphatidylinositol linked, the cells were treated with a phosphatidylinositol specific phospholipase C. Under conditions where a PI-linked antigen, LFA-3, could be released [A. Peterson et al., "Monoclonal Antibody And Ligand Binding Sites Of The T Cell Erythrocyte Receptor (CD2)," *Nature,* 329:842 (1987)], no effect was observed on the LT-α epitope.

We could not stain CHO cells stably transfected with the LT-α gene, either with or without prior PMA activation, indicating that antibodies to CHO derived contaminants in the original rLT-α used to immunize the rabbits were not present in sufficient amounts to contribute to the staining of II-23.D7 cells. Likewise, antibodies generated against any fetal bovine serum proteins contaminating the LT-α preparation would be ineffective in staining T cells since the staining was performed in 10% fetal calf serum.

Pretreatment of the anti-rLT-α serum with rLT-α blocked the staining of LT-α forms on II-23.D7 cells whereas pretreatment with rTNF did not.

Example 2
Immunoprecipitation of LT-α-Related Proteins on the T Cell Hybridoma II-23.D7

Figure 4A:
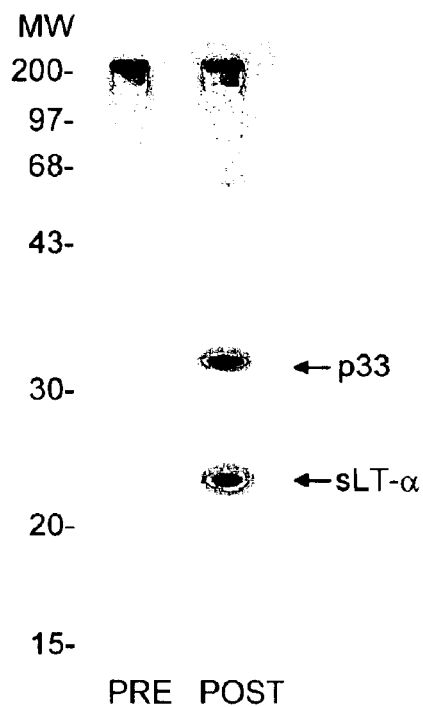
FIG. 4A shows immunoprecipitation of an approximately 25 kD surface protein (LT-α) and an approximately 33 kD surface protein (p33, or LT-β) by post-immune rabbit anti-rLT-α antiserum but not by pre-immune rabbit serum.

We surface iodinated PMA activated II-23.D7 cells and lysed and solubilized the cells in detergent. Immunoprecipitation and SDS-PAGE analysis of the labeled membrane proteins showed that two proteins were recognized by anti-rLT-α antisera. FIG. 4A shows the results of SDS-PAGE analysis of the iodinated surface proteins precipitated with either pre-immune (PRE) or post-immune (POST) anti-rLT-α serum (from rabbit 4).

As shown in FIG. 4A, we observed a 25–26 kD molecular weight form ("LT-α") that correlated with the expected size of LT-α, and we also saw an additional form of approximately 33 kD ("LT-β or p33"). Neither the preimmune serum from the same rabbit (FIG. 4A column PRE) nor anti-rTNF rabbit serum were able to immunoprecipitate any bands from the iodinated, PMA-activated II-23.D7 cells.

Figure 4B:
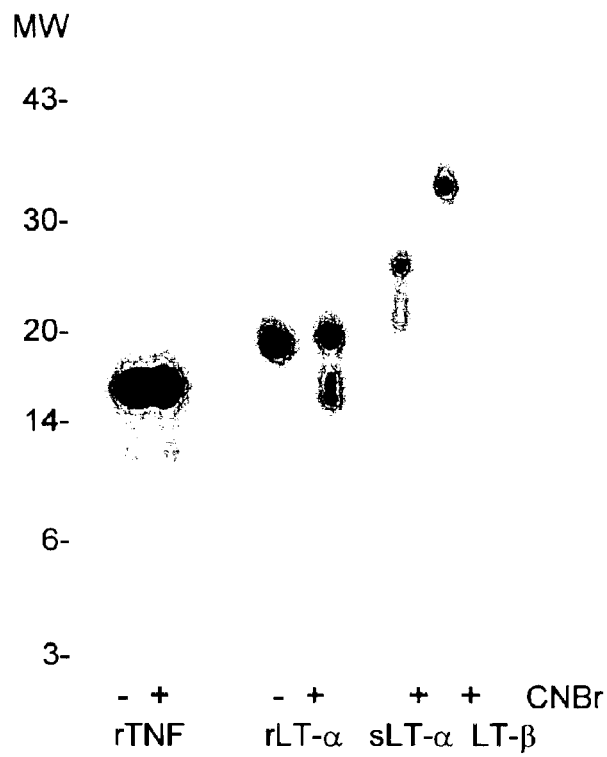
FIG. 4B shows a 1-dimensional CNBr cleavage map of the 25 kD and 33 kD bands from FIG. 4A, compared against recombinant TNF (rTNF) produced in *E. coli*, and recombinant lymphotoxin-α (rLT-α) produced in CHO cells, [J. Browning et al., *J. Immunol.*, 143:1859 (1989)] both with (+) and without (−) CNBr cleavage.

1-D partial CNBr peptide mapping of the iodinated bands showed that the 25–26 kD form was cleaved in a pattern identical to that of iodinated rLT-α, thus identifying this band as LT-α. In the experiment shown in FIG. 4B, the 25–26 kD and 33 kD bands from panel A were excised, subjected to limited CNBr cleavage and electrophoresed on a SDS-PAGE system. For comparison, cleavages of both rTNF and rLT-α performed in parallel are shown in FIG. 4B. The gels were visualized by autoradiography. Lane 1 represents rTNF, lane 2 represents rLT, lane 3 represents LT, and lane 4 represents LT-β. The increased sizes of the CNBr fragments reflect the increased amount of carbohydrate on natural LT-β. The iodinated 33 kD form was not cleaved by CNBr (lane 4), indicating that it is different from the known LT-α gene product. rTNF was not cleaved with CNBr (lane 1) due to the absence of methionine in this protein.

Figure 5:
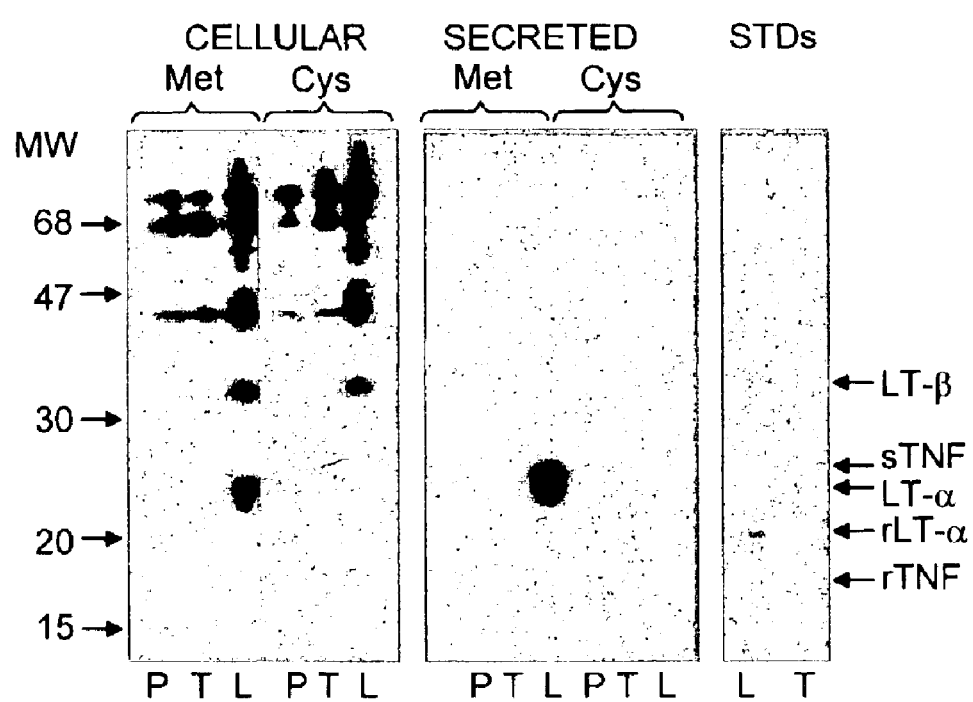
FIG. 5 presents autoradiographs showing immunoprecipitation of TNF- and LT-α-related proteins from PMA-stimulated II-23.D7 cells metabolically labeled with $^{35}$S-methionine or $^{35}$S-cysteine. The figure shows recognition by anti-rLT-α antisera (L), but not preimmune (P) or anti-rTNF antisera (T), of an approximately 25 kD methionine-containing surface protein (LT-α) and an approximately 33 kD methionine- and cysteine-containing surface protein (p33, or LT-β). The autoradiographs also indicate that activated II-23.D7 cells also produce a 26 kD form of TNF and secrete soluble lymphotoxin-α.

We undertook metabolic labelling with $^{35}$S-methionine and $^{35}$S-cysteine coupled with immunoprecipitation to characterize further these LT-α-related surface forms. In the case of the TNF/LT-α pair, the distribution of cysteine and methionine allows one to distinguish both between TNF and LT-α and between forms with and without their signal sequences, as was exploited in studies on the membrane TNF form [M. Kriegler et al., Cell, 53:45–53 (1988)]. In the case of the fully processed cytokines, i.e., secreted forms, TNF contains cysteine and not methionine, while LT-α contains only methionine and not cysteine. LT-α, however, has two cysteine residues in the signal sequence domain and TNF contains a methionine residue in this N-terminal region. Separate cultures of II-23.D7 hybridoma cells were labeled with either $^{35}$S-methionine or $^{35}$S-cysteine and immunoreactive proteins were precipitated. In an experiment, the results of which are shown in FIG. 5, II-23.D7 cells were activated with 10 ng/ml PMA and simultaneously labeled for 8 hours with either $^{35}$S-methionine or $^{35}$S-cysteine. Both the medium and lysed cells were subjected to consecutive immunoprecipitations with preimmune (rabbit 4) (P), anti-rTNF (T) and anti-rLT-α (rabbit 4) (L) sera in that order. FIG. 5 shows an SDS-PAGE auto-radiographic analysis of the immunoprecipitates from either supernatants containing secreted proteins or the washed cells. "s-TNF" marks the $^{35}$S-methionine labeled anti-rTNF immunoprecipitated band from the cells that was putatively assigned as the unprocessed 26 kD form of TNF. "Met" and "Cys" refer to the $^{35}$S-labeled amino acid employed. Those lanes containing $^{35}$S-cysteine were exposed for longer periods of time than the lanes containing $^{35}$S-methionine. In the supernatants from these cells (lanes labeled "secreted"), a 25 kD form of LT ("LT-α") was released following PMA treatments by those cells that were labeled with $^{35}$S-methionine, but not by those labeled with $^{35}$S-cysteine. This pattern is expected for fully processed, secreted LT-α. Longer exposures showed trace amounts of TNF in the supernatant, and the incorporation of label was as expected for fully processed, secreted TNF. We observed the expression of predominantly LT-α with low levels of TNF also at the mRNA level (Shamansky and Ware, unpublished observation). Analysis of the washed cells (lanes labeled "cellular") showed that both the 25–26 kD LT-α, along with the 33 kD LT-β, were present. The relative amounts of the 25–26 kD and 33 kD forms paralleled those observed using surface iodination. The 25–26 kD surface LT-α form lacked cysteine, indicating processing of the leader sequence. The 33 kD form incorporated both $^{35}$S-methionine and $^{35}$S-cysteine. Longer exposures (not shown) of the film shown in FIG. 5 revealed the presence of an anti-TNF immunoprecipitated band from the cells at about 26–27 kD. The band showed incorporation of both labeled cysteine and labeled methionine. The labelling was stronger with cysteine. Since the cys:met ratio is 4:1 in the 26 kD-TNF form, this labelling pattern confirms the identity of this band.

The presence of LT-β with LT-α in immunoprecipitates from cell lysates suggested that either LT-β is antigenically related to LT-α or that LT-β is bound to LT-α or both. To address this issue 25 kD and 33 kD bands from $^{35}$S-methionine labeled cells were immunoprecipitated with rabbit polyclonal anti-rLT-α serum, eluted from excised gel slices and subjected to reimmunoprecipitation with either anti-rLT-α polyclonal serum or mAb. LT-α, but not LT-β, could be immunoprecipitated with either anti-rLT-α antibodies suggesting that LT-β is not antigenically related to LT-α. These observations indicated that LT-β is physically associated with LT-α. We believe that the 33 kD protein is unrelated antigenically to LT-α and simply co-precipitated with LT-α.

With either surface iodination or metabolic labelling, we were unable to detect either of the known 55 or 80 kD TNF/LT-α receptor forms associated with LT-α or TNF. Presumably, this is because the receptors are rapidly lost during activation of T cells. [C. Ware et al., "Regulation Of The CTL Lytic Pathway By Tumor Necrosis Factor," *Cellular Immunity And The Immunotherapy Of Cancer*, UCLA Symposia on Molecular and Cell Biology M. T. Lotze and O. J. Finn, Eds. Vol. 135:121–128 (Wiley-Liss, Inc. New York) 1990].

Example 3

Biochemical Characterization of Surface LT-Forms on II-23.D7 Cells

We purified the LT-related forms on the surface of PMA-treated II-23.D7 cells using affinity chromatography. Using immunoprecipitation techniques, we had noted that both of LT-β and LT-α bound to lentil lectin sepharose, indicating a glycoprotein structure. We bound detergent solubilized PMA-treated II-23.D7 proteins to lentil lectin sepharose and eluted with á-methyl mannoside prior to affinity purification. We prepared both control IgG and anti-IgG columns to more accurately assess those proteins specifically recognized by the anti-rLT-α serum. Low pH elution of the columns led to the release of about 100–200 ng of the two LT forms from the anti-rLT-α column.

Figure 6A:
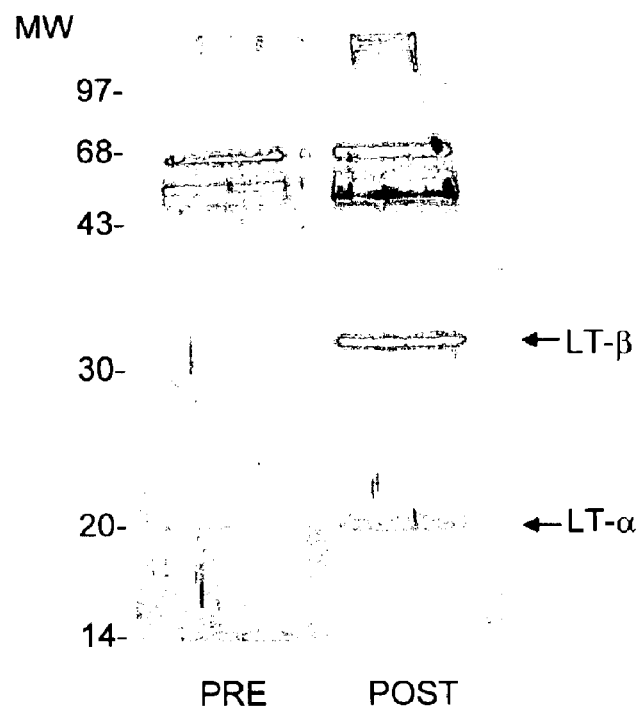
FIG. 6A represents SDS PAGE analysis of the proteins eluted from an anti-LT-α affinity column prepared from either pre-immune (PRE) or post-immune (POST) rabbit sera.
Figure 6B:
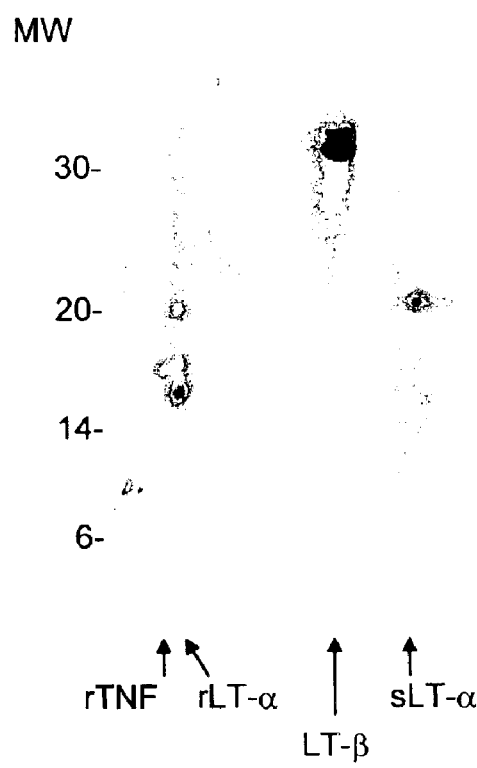
FIG. 6B shows partial CNBr cleavage of the ⁻33 kD and ⁻20 kD proteins eluted from the POST column, compared against rTNF and rLT-α run in parallel. The gels were visualized by silver staining.

FIG. 6A reflects SDS PAGE analysis of the proteins eluted from anti-rLT-α affinity column prepared from either pre-immune (PRE) or post-immune (POST) rabbit sera. In FIG. 6B, the 33 kD and 20 kD bands from the gel in panel A were excised and subjected to limiting CNBr cleavage and electrophoresed on a SDS-PAGE system. For comparison, FIG. 6B showed CNBr cleavages of rTNF and rLT-α (CHO-derived) performed in parallel. The gels were visualized by silver staining. SDS-PAGE gels of the eluate resembled closely gels of immunoprecipitated, surface iodinated PMA-treated II-23.D7 cells, indicating that similar proteins had been purified.

During the affinity purification, the 25 kD LT-α form appeared to be cleaved to a 19–20 kD form, i.e., it now co-migrated with the intact recombinant CHO cell-derived LT-α. The original isolation of natural LT-α from the RPMI 1788 tumor line also yielded an N-terminally cleaved "des-20" LT-α form. One-dimensional CNBr digests of the affinity purified proteins showed the cleaved 20 kD LT-α form to have a CNBr cleavage pattern that presumably reflects the truncated nature of this LT-α form. One of the methionines is lost in the "des-20" LT-α form and hence the cleavage pattern would be different from that of the intact LT-α form. The 33 kD protein (LT-β) generated a doublet upon CNBr cleavage, and from this it was estimated that the single methionine must lie within 5–20 residues from either the C- or N-terminus. This cleavage pattern shows that the 33 kD protein is significantly different from known LT forms. CNBr cleavage analysis of the surface iodinated 33 kD protein probably gave a similar result; however, the resolution achievable with iodination was insufficient to visualize the doublet. Staphylococcus V8 digestion of the iodinated rLT-α, rTNF and II-23.D7 LT forms showed the rLT-α and 25–26 kD II-23.D7 LT-α form to be resistant to digestion, confirming the assignment of this protein as LT-α. The 33 kD protein was cleaved into several smaller fragments with the pattern resembling closely that of rTNF.

Figure 7:
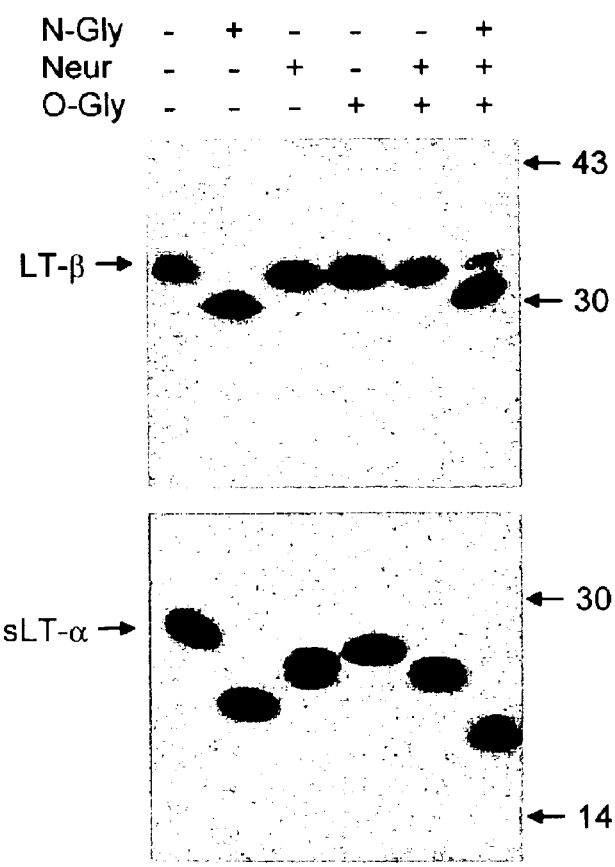
FIG. 7 presents autoradiographs of the ⁻25 kD and ⁻33 kD $^{125}$I-labeled proteins (designated LT-α and LT-β, respectively) immunoprecipitated from activated II-23.D7 cells, treated with N-glycanase (N-gly), with a mixture of neuraminidase and O-glycanase (O-gly), or with all three enzymes.

In FIG. 7, immunoprecipitated, surface iodinated proteins were resolved on SDS-PAGE analysis and the surface-associated 25–26 kD protein ("sLT-α") and the 33 kD protein ("LT-β") bands were excised. Slices were digested with N-glycanase (N-Gly), with a mixture of neuraminidase and O-glycanase (O-Gly), or with all three enzymes. The digested slices were rerun on SDS-PAGE and an autoradiogram of the dried gel is shown. As shown in FIG. 7, immunoprecipitation of iodinated surface LT forms followed by digestion with either or both N- and O-glycanases showed the 25–26 kD LT-α form to contain an N-linked oligosaccharide. The 25–26 kD LT-α form contains only one N-linked site which would correlate well with the size change upon N-glycanase digestion. Likewise, the 33 kD form (LT-β) lost about 3 kD of size upon treatment with N-glycanase, suggesting the presence of one N-linked oligosaccharide. In contrast to the 25–26 kD LT-α form, O-glycanase treatment did not affect the molecular weight of LT-β. The lack of cleavage by a glycanase, however, is not definitive evidence for the lack of a carbohydrate.

Example 4

Reimmunoprecipitation of LT-α

Figure 10B:
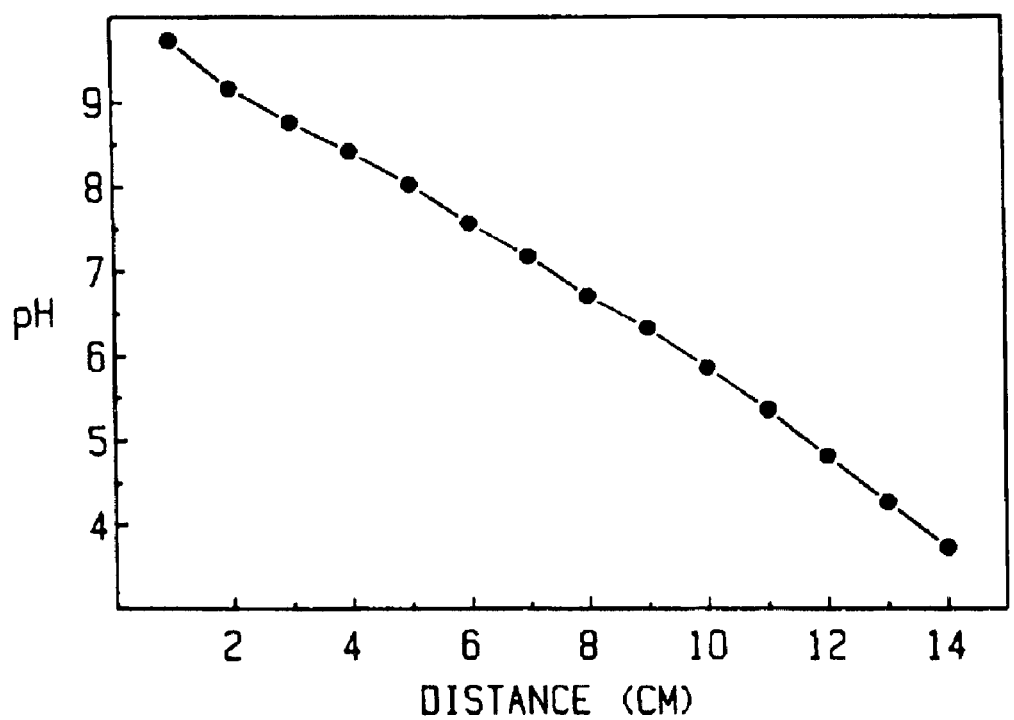
Figure 11A:
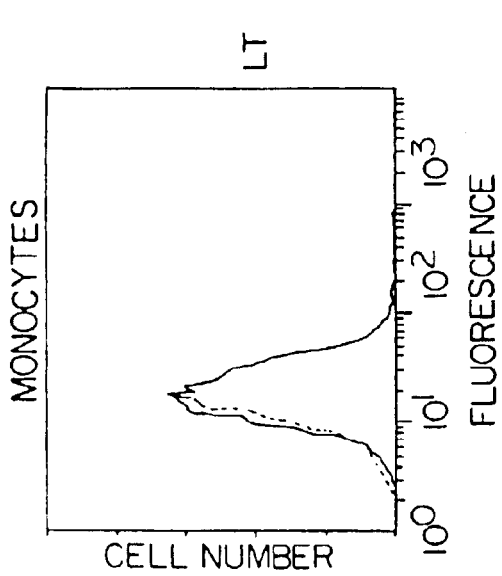
FIG. 11 depicts flow cytofluorometric analysis of surface proteins differentially expressed on T cells and monocytes after stimulation with a mixture of LPS, IFN-γ and OKT3. From a stimulated PBL pool, separated T cells were observed to express a surface protein recognized by anti-rLT-α antisera (LT), whereas separated monocytes expressed a surface protein recognized by anti-rTNF antisera (TNF).
Figure 11B:
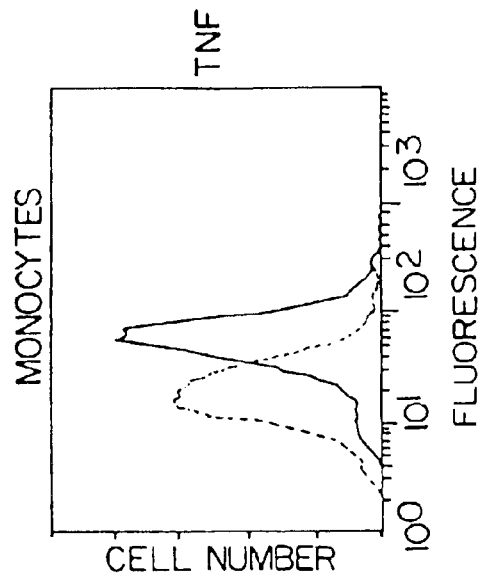
Figure 11C:
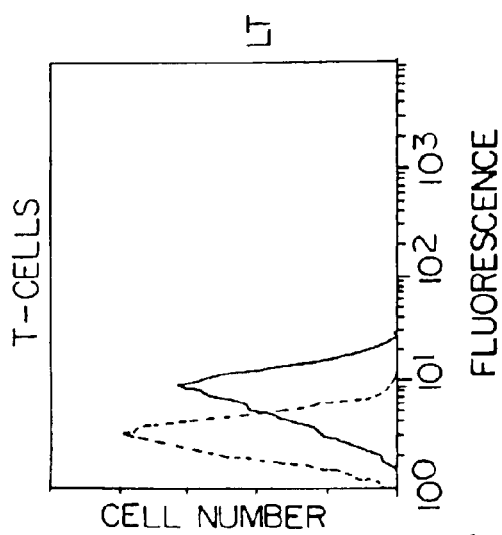
Figure 11D:
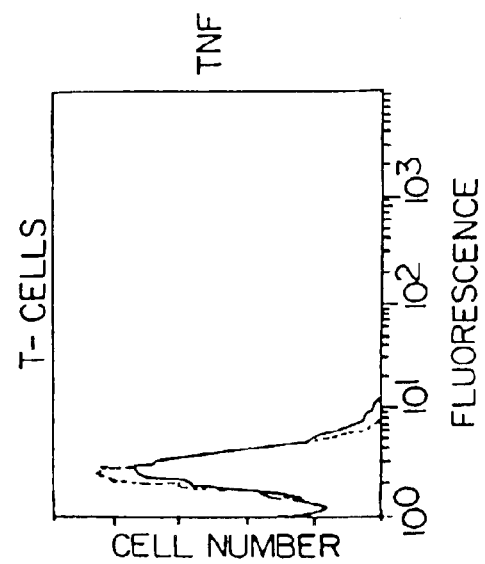

The coprecipitation of LT-β with LT-α suggested that these proteins are either antigenically related or physically associated. To address this issue we tested whether or not SDS-PAGE separated LT-α (p25) and LT-β proteins could be immunoprecipitated. LT-α and LT-β labeled with $^{125}$I or $^{35}$S-Met were first partially purified by immunoprecipitation and separated by SDS-PAGE. The labeled bands were excised, rehydrated in buffer, and the proteins eluted. The eluted proteins were then subjected to a second round of immunoprecipitation using either polyclonal or monoclonal anti-rLT-α antibodies (FIG. 10). Rabbit anti-rLT-α reimmunoprecipitated LT-α ("p25", lane 2) but not LT-β (lane 3). The anti-rLT-α mAb precipitated LT-α (lane 5) and a 21 kD protein ("p21", lane 4), which, as shown below, is a precursor of LT-α; however, it did not precipitate LT-β (lane 6). The results indicate that after LT-α and LT-β are separated by SDS-PAGE, both polyclonal and monoclonal anti-rLT-α antibodies are capable of reacting with LT-α but not with LT-β. This data provides evidence that LT-β is not antigenically related to LT-α. However, we cannot rule out the possibility that putative LT-β cross-reactive epitopes are lost after denaturation, whereas the LT-α epitopes remain intact.

Figure 8:
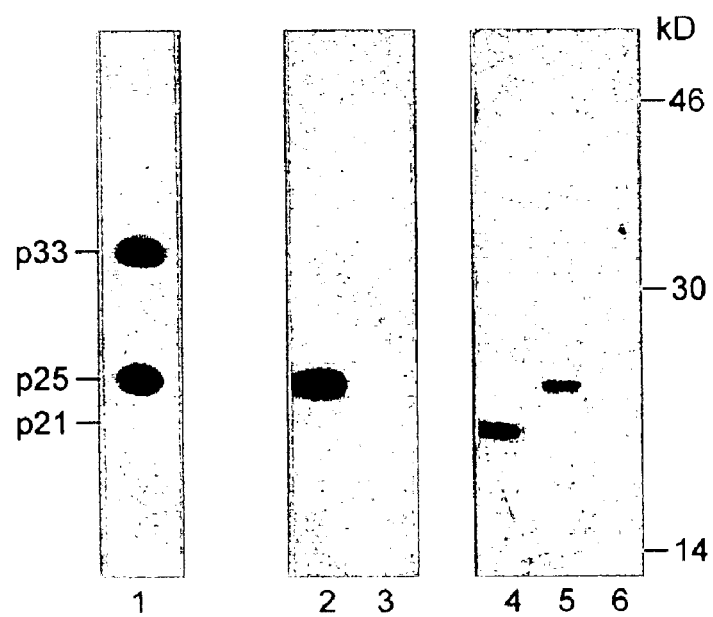
FIG. 8 depicts the results of a reimmunoprecipitation of the coprecipitated p33 (LT-β) and p25 (LT-α) proteins to further investigate whether they are immunogenically related.

FIG. 8 shows the results of reimmuno- precipitation of $^{125}$I-labeled and $^{35}$S-Met-labeled p25 and p33 proteins eluted from SDS-PAGE gels. LT-α and LT-β species from $^{125}$I-labeled II-23.D7 cells (lanes 2,3) and $^{35}$S-labeled cells (lanes 4,5,6) were eluted from gel slices as described above. The elutes were immunoprecipitated with either the anti-rLT-α serum (lanes 2,3) or the anti-rLT-α mAb (lanes 4,5,6), and the reprecipitated proteins analyzed by SDS-PAGE and autoradiography. Lane 1 is a control lane for the identification of LT-α and LT-β.

Example 5

Isoelectric Focusing of LT-α and LT-β

Figure 9B:
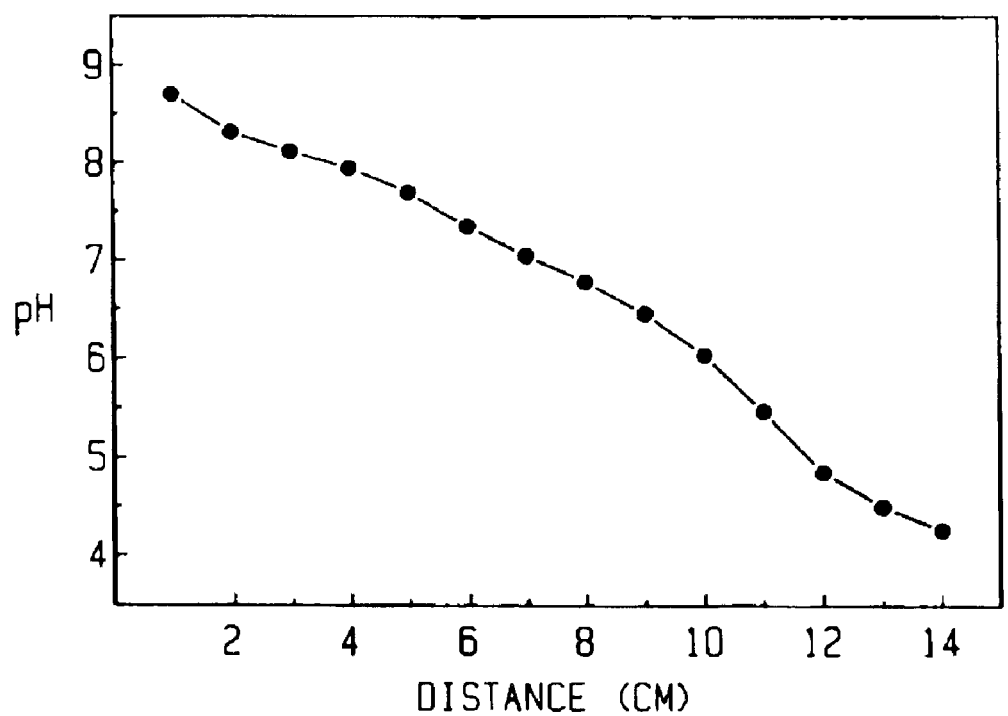

FIGS. 9 and 10 (each including an autoradiograph (9A, 10A) and a calibration curve graphing migration distance vs. pH (9B, 10B)) depict isoelectric focusing analysis under denaturing (FIG. 9) and native (FIG. 10) conditions. Two-dimensional gel analysis was carried out as described above on $^{125}$I-labeled LT-α and LT-β that had been immunoprecipitated from II-23.D7 cell extracts. The 2-D gel analysis was performed under denaturing conditions in the presence of urea (FIG. 9A). In contrast, native IEF was performed in 1% NP-40 without urea. $^{125}$I-labeled II-23.D7 cell extract was first focused on a tube gel at 4°. After focusing, the tube gel was cut into 1 cm sections, the focused proteins eluted from those sections, immunoprecipitated, and analyzed by SDS-PAGE (FIG. 10A). Immunoprecipitated material from gel lanes 1–12 correspond to tube gel slices 2–13. pH gradients were generated for both the denatured and native tube gels based on 1 cm gel increments. These are also shown below each autoradiogram as 9B and 10B, respectively. Biochemically, LT-B and LT-α comigrate on a non-denaturing isoelectric focusing gel, but when the complex is dissociated with urea, the two proteins run separately. [See FIGS. 9A, 10A] These observations led us to conclude that LT-α and LT-β exist as a complex on the cell surface.

Example 6

Regulation of LT-α Expression

Table I set forth below, summarizes the results of a survey using flow cytofluorometric analysis of various cell types for the expression of a surface form of LT-α.

TABLE I

Expression of LT-α and TNF Related Epitopes on the Surfaces of Different Cells

| Cell | Treatment | Surface Expression of: | |
|---|---|---|---|
| | | LT-α | TNF |
| Peripheral Mononuclear cells | Resting | + | − |
| | OKT3 | ++ | − |
| Leu-4+ (CD3) | Resting | + | − |
| | OKT3 | ++ | − |
| | PMA | − | nd. |
| | IL-2 | ++ | nd. |
| Leu-2+ (CD8) | OKT3 | ++ | nd. |
| Leu-3+ (CD4) | OKT3 | ++ | nd. |
| Leu-M3 | Resting | − | + |
| | OKT3/LPS/IFN-γ | − | ++ |
| Leu-19+ (NK) | IL-2 (LAKs) | ++ | nd. |
| Leu-16+ (B's) | Resting | +/− | − |
| | PWM | + | nd. |
| CTL-clones | Control | +/− | − |
| | PMA | nd. | nd. |
| | Allogeneic Stim. | ++ | nd. |
| | Anti-T11 2 + 3 | ++ | − |

TABLE I-continued

Expression of LT-α and TNF Related
Epitopes on the Surfaces of Different Cells

| Cell | Treatment | Surface Expression of: LT-α | TNF |
|---|---|---|---|
| T cell Hybridoma (II-23.D7) | Control | – | – |
|  | PMA | ++ | – |
|  | PMA + A23187 | ++ | – |
| Hut-78 | Control | + | – |
|  | PMA | + | – |
| C8166 | Control | – | nd. |
|  | PMA | + | nd |
| RPMI-1788 | Control | – | – |
|  | PMA | – | – |
| rLT-producing CHO cell line | Control | – | – |
|  | PMA | – | – |
| Jurkat |  | +/– | nd. |
| HL-60 |  | – | – |
| U937 |  | – | nd. |
| Raji |  | + | nd. |
| K562 |  | +/– | nd. |

The most striking observation from these studies was the restriction of surface LT-α expression to T and B cells. Leu-M3, a monocyte marker, and leu-4 (CD3) antibodies were used in two-color flow cytofluorometric analysis to observe each cell population separately. There was an excellent distinction between surface TNF and surface LT-α in this analysis in that monocytes expressed only surface TNF whereas T cells displayed only surface LT-α. This result is shown in FIG. 11.

In the experiment depicted in FIG. 11, PBL were treated for 8 hours with a mixture of LPS (1 μg/ml), Interferon-γ (200 U/ml) and OKT3 (1 ng/ml) and then stained for LT-α (anti-rLT-α serum from rabbit 5) or TNF (anti-rTNF serum from rabbit 7) followed by FITC anti-rabbit labelling. Cells were counterstained with either phycoerythrin-leu-4, a pan T cell marker, or phycoerythrin leu-M3, a monocyte marker. "T cell panels" were gated for leu-4+ cells while the "monocyte" panels were gated for leu-M3+ cells. Cells were stained with preimmune (dotted lines) or postimmune sera (solid lines). The monocytic tumor lines HL-60 and U937 did not stain for LT-α. By using two color flow cytofluorometric analysis, the T4 and T8 subclasses of activated PBL were found to display similar levels of surface-associated LT-α. In general, it appears that primary T-cells capable of expressing LT-α are also capable of displaying surface LT-α form(s).

Examination of three different human donors showed that a surface LT-α form was present on freshly isolated, resting peripheral T cells. In the case of PBL, OKT3 activation or simply IL-2 treatment of the cells led to increased expression. By using fluorescence channel numbers, we have attempted to quantitate both surface LT-α and IL-2 receptor (CD25) expression during OKT3 activation. Maximal surface LT-α induction by OKT3 appeared to precede the peak expression of IL-2 receptor (TAC expression) in the bulk culture, thus the surface-bound LT form (LT-α/LT-β complex) appears to be an early T-cell activation antigen. It was found that both anti-T11 and allogeneic antigen were capable of causing the appearance of LT-α on the surface of cloned cytotoxic T cells. Likewise, PMA stimulation was necessary to induce the appearance of LT-α on the surface of the II-23.D7 hybridoma. It appears that T cell activation increases surface LT-α form(s). Peripheral lymphocytes, in contrast to the II-23.D7 hybridoma, down-regulate surface LT-α form(s) very quickly following PMA treatment. Likewise, in a two-color analysis of OKT3 activated PBL populations, Dr+ cells, which should include T cells in advanced stages of activation, lacked surface LT-α form(s).

Figure 12A:
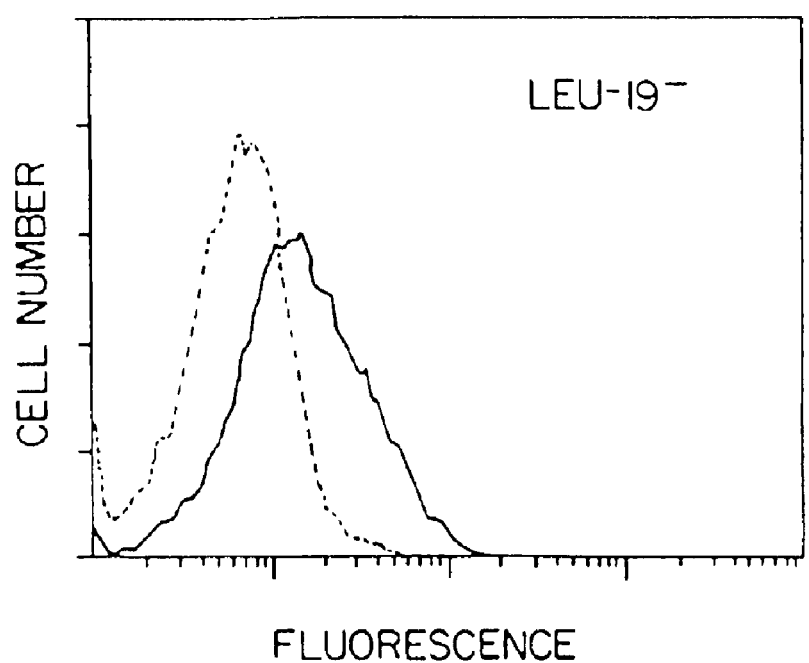
FIG. 12 shows flow cytofluorometric analysis of surface LT forms on leu-19⁻ and leu-19⁺ (i.e., natural killer) cells treated with IL-2. Analysis of IL-2 treated PBL with both labeled leu-19 and anti-rLT-α confirms that lymphokine-activated killer (LAK) cells express a surface LT form.
Figure 12B:
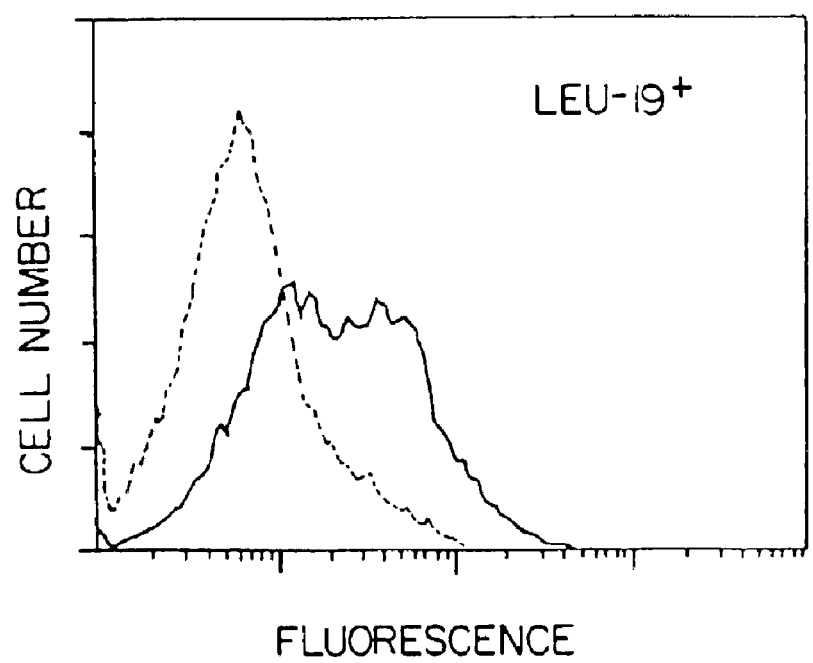

Activation of fresh PBL with high levels of IL-2 generated lymphokine-activated killer cells (LAK cells). As shown in FIG. 12, two color flow cytofluorometric analysis using anti-rLT-α and leu-19, a NK/LAK cell marker, showed LAK cell expression of surface LT-α forms to resemble the T cell hybridoma, II-23.D7. In the experiment depicted in FIG. 12, PBL were cultured for 5 days with 20 ng/ml IL-2 and then stained for a two color analysis with phycoerythrin labeled leu-19 and anti-rLT (rabbit 5) as described above. FIG. 12 shows surface LT-α levels on leu-19+ cells that were stained with preimmune (dotted lines) or postimmune sera (solid lines). Thus, LAK cells appeared to have the highest levels of surface LT-α forms of any primary cell type.

Example 7

Functional Relevance of Total TNF or LT-α to T Cell Activation

To examine the functional relevance of TNF and LT-α to the T cell activation process, we included the rabbit anti-rLT-α and anti-rTNF sera in mixed lymphocyte response (MLR) and OKT3 activation assays. MLR is a standard immunological assay which tests the ability of an individual's T cells to recognize another person's T cells as foreign and respond to their presence by proliferating. Table II, set forth below, presents data from MLR experiments using various responder/stimulator combinations.

TABLE II

Effects of LT and TNF Antibodies on a 5-Day Mixed Lymphocyte Culture

| Cells[b] | Addition | $^3$H-Thy. (S.D.) cpm × 1000 | % Change[a] |
|---|---|---|---|
| Responder A | none | 4.7 (0.8) | – |
| Stimulator B* | none | 4.8 (0.5) | – |
| A + B* | none | 20.3 (3.6) | 0% |
| A + B* | r-TNF[c] | 28.0 (1.4) | +49% |
| A + B* | r-LT | 32.8 (3.2) | +80% |
| Responder C | none | 6.3 (0.8) | – |
| Stimulator B* | none | 4.8 (0.7) | – |
| C + B* | none | 30.0 (5.4) | 0% |
| C + B* | r-TNF | 36.9 (6.0) | +28% |
| C + B* | r-LT | 36.1 (5.8) | +24% |
| Responder A | none | 5.3 (0.6) | – |
| Stimulator D* | none | 1.5 (0.5) | – |
| A + D* | none | 22.2 (2.6) | 0% |
| Responder D | none | 7.8 (1.0) | – |
| Stimulator A* | none | 1.6 (0.3) | – |
| D + A* | none | 24.3 (7.0) | 0% |

|  |  | Preimmune | Postimmune |
|---|---|---|---|
| A + B* | Anti-LT-4[d] | 26.8 (2.4) +41% | 8.6 (0.2) –74% |
| A + B* | Anti-LT-5 | 27.4 (4.4) +45% | 11.0 (1.2) –59% |
| A + B* | Anti-LT-6 | 23.1 (1.0) +18% | 25.7 (5.7) +35% |
| A + B* | Anti-TNF | 26.0 (2.2) +36% | 12.6 (2.7) –49% |
| A + B* | Anti-TNF mAb* | 15.1 (2.2) –33% | 4.7 (0.7) –99% |
| C + B* | Anti-LT-4[d] | 41.1 (3.5) +44% | 20.9 (5.8) –36% |
| C + B* | Anti-LT-5 | 35.5 (6.9) +22% | 17.8 (2.6) –49% |
| C + B* | Anti-LT-6 | 39.4 (7.9) +38% | 39.1 (5.3) +36% |
| C + B* | Anti-TNF | 39.8 (4.3) +39% | 24.4 (3.2) –22% |
| C + B* | Anti-TNF mAb[e] | 37.8 (7.3) +31% | 20.6 (1.8) –37% |
| A + D* | Anti-LT-5 | 28.6 (2.1) +37% | 12.5 (2.4) –59% |
| A + D* | Anti-LT-5 | 32.8 (6.4) +63% | 14.5 (3.6) –47% |

TABLE II-continued

Effects of LT and TNF Antibodies
on a 5-Day Mixed Lymphocyte Culture

| Cells[b] | Addition | $^3$H-Thy. (S.D.) % Change[a] cpm × 1000 | |
|---|---|---|---|
| D + A* | Anti-LT-5 | 28.0 (1.2) +23% | 20.8 (1.4) −21% |
| D + A* | Anti-LT-5[f] | 28.1 (2.1) +24% | 19.2 (0.7) −31% |

See notes below.
[a]Percent change refers to the increase or decrease in $^3$H-thymidine incorporation after correction for a background of responder cells alone.
[b]Stimulator cells were irradiated with 3000 rads and are denoted with a "*". Low level proliferation was still evident in stimulator population. The ratio of responder to stimulator was 1/1.5.
[c]rTNF and rLT were added to a level of 10 ng/ml.
[d]Antisera were heat inactivated for 1 hour at 56° C., filtered and used at a final dilution of 1:250.
[e]The monoclonal anti-TNF was a purified mouse IgG$_{2a}$ antibody used at 2 μg/ml and the control in this case was pure mouse UPC 10 (IgG$_{2a}$).
[f]In these cases, the immunoglobulin fraction was purified from the serum and used at a final concentration of 50 μg/ml.

As shown in Table II, the neutralizing anti-rLT-α sera (rabbits 4 and 5) inhibited the proliferative response as assessed at five days whereas preimmune sera or the non-neutralizing anti-rLT-α (rabbit 6) sera had mild stimulatory effects. As previously reported [M. Shalaby et al., *J. Immunol.*, 141:499 (1988)], polyclonal and a monoclonal anti-TNF preparations were also inhibitory. These assays were carried out under excess stimulator cell conditions and hence the inhibition may not be optimized. The serum levels employed in Table II are rather high, but in other experiments (data not shown), antibody dilutions up to 1:1000 were still inhibitory. PHA or OKT3 stimulated T cell proliferation was also inhibited to a lesser extent (data not shown). These data indicated that LT or LT-related epitopes on T cell surfaces may be involved in T cell activation.

A previous study using the MLR assay and neutralizing monoclonal antibodies implicated TNF but not LT-α in T cell activation and subsequent proliferation in this system. [M. Shalaby et al., *J. Immunol.*, 141:499 (1988)]. In that study, monoclonal anti-rLT-α antibodies had no effect on the MLR assay. Our studies indicate that neutralizing polyclonal anti-CHO-cell-derived-rLT-α sera were able to partially inhibit the MLR, suggesting a role for some form of LT in this system. The reasons for this discrepancy are not clear, although there may be some differences in the nature of these antibody preparations. The monoclonal antibodies were generated against glutaraldehyde-cross linked natural LT-α (RPMI 1788 secreted), whereas polyclonal anti-rLT-αsera were prepared using native r-LT-α (recombinant CHO-cell derived) with Freund's adjuvant injected directly into the lymph nodes. The depot effect in the success of the latter system was probably important considering the difficulties reported in immunizing mice [T. Bringman et al., "Monoclonal Antibodies to Human Tumor Necrosis Factors Alpha and Beta: Application For Affinity Purification, Immunoassays, And As Structural Probes," *Hybridoma*, 6:489 (1987)]. These data suggest that the blocking effect of our polyclonal anti-rLT-α sera on the MLR is a result of recognition of the surface LT form(s) by the sera rather than recognition of the conventional soluble LT-α form.

Example 8
Purification and Initial Sequencing Of LT-α and LT-β

We obtained N-terminal sequence information for LT-α and LT-β by Edman degradation as described above. We found the sequence of the membrane associated LT-α band to be as follows: Leu Pro Gly Val Gly Leu Thr Pro Ser. This sequence matches with the known sequence of secreted LT-α. The Edman degradation analysis revealed that the N-terminal portion of the associated LT-β protein included two possible amino acid sequences: Gly Leu Glu Gly Arg Gly Gln Arg Leu Gln or Gly Leu Glu Gly Arg Leu Gln Arg Leu Gln. Subsequent DNA analysis confirmed the former sequence except that glycine was incorrectly identified as glutamine at cycle 7.

Example 9
Sequencing and Cloning LT-β

As described above, we obtained sequences for several peptides using the method of Abersold et al. Two antisense 17-mer oligonucleotide probes GTYTCNGGCTCYTCYTC [SEQ ID NO:9] and GTYTCNGGTTCYTCYTC [SEQ ID NO:10] were synthesized to match a portion of the sequence of one of those peptides, T-87/T-88. Those probes were radiolabelled with $^{32}$P. Northern analysis (as described in J. Sambrook et al., *Molecular Cloning a Laboratory Manual*, 2d ed. (1989)) showed that probe 1368 (GTYTCNGGTCYTCYTC) [SEQ ID NO:10] hybridized strongly to a 0.9–1.1 kb mRNA band that was strongly induced in II-23.D7 cells which had been pretreated with phorbol ester as previously described. A cDNA library in the vector pCDM8 was constructed from poly A+ mRNA isolated from II-23.D7 cells induced with PMA for 6 hours. [See, B. Seed and A. Aruffo, *PNAS*, 84:3365–3369 (1987)]. The library was screened with labelled oligomer 1368 and positive clones were isolated following washing with 3 M tetramethylammonium chloride at 50° C. [See Jacobs et al., *Nucleic Acids Research*, 16, 10:4637–4649 (1988)]. Several clones containing 0.9 kb inserts were subjected to DNA sequence analysis. Clone pCDM8/LT-β-12 (clone 12) was found to contain the coding sequence. The other clones were identical except for various 1–30 bp truncations at the 5' end. One potential clone (clone 4) contained a frameshift and was used as a control in transfection experiments. A termination sequence, AATAAA at position 862 was found just prior to a poly A tract indicating that the entire 3' end had been identified. The identified protein sequence encodes for at least 240 amino acids with a calculated molecular weight of 25,390 and a domain structure typical of a type II membrane protein. The present data suggest that the initiating CTG leads to a processed N-terminus starting with gly 5 (met=1), i.e., the CTG encoded leucine is either not translated or the leucine-4 residue is further processed yielding the mature N-terminus obtained by amino acid sequencing.

The 33 kDa size of LT-β results from N-linked glycosylation as previously defined and this result is corroborated by the presence of one potential N-linked carbohydrate site in the amino acid sequence at a position identical with a similar site found in the CD40 ligand. A typical N-linked sugar residue can add approximately 3–4 kDa MW, hence, the final molecular weight is close to the observed 30–33 kDa.

No identical sequences were found within the databases. There is one cysteine residue in the extracellular domain and two methionines within the last C-terminal 17 amino acids, in agreement with the very limited cyanogen bromide cleavage pattern exhibited by this protein.

Example 10
Expression of LT-β

The pCDM8/LT-β clone 12 or a control plasmid, clone 4 (pCDM8 with a non-functional cDNA insert), were introduced by electroporation into CHO dhfr- and a CHO cell stably transfected with human LT-α. After three days, cells were removed with Ca/Mg-free Hank's solution with 5 mM EDTA and stained for FACS analysis as described above using either 10 µg/nl control IgG1 or anti-LT monoclonal antibody (Boehringer-Mannheim) followed by labelling of bound immunoglobulin with either a FITC or phycoerythrin labelled goat anti-mouse preparation.

In a different experiment, COS cells were electroporated with either clone 4 or clone 12 LT-β cDNA in pCDM8 in the presence or absence of an equal amount of human LT-α cDNA also in the pCDM8 vector and stained for FACS analysis after three days as above. Only COS cells expressing LT-α displayed surface lymphotoxin upon transfection with a functional LT-β DNA, i.e., clone 12.

Clone 12 lacks an initiating ATG codon, but does possess several CTG initiating codons and hence this expression experiment shows that one or several of the 5' CTG codons can initiate translation. CTG codons are known to serve as initiating sites for translation in several eukaryotic proteins. [M. Kozak, *J. Cell. Biol.*, 115:4 (1991)]. Similar results were observed using the dual transfection system such that only COS cells receiving both LT-α and LT-β DNA displayed substantial surface LT-α in a FACS analysis.

Figure 15A:
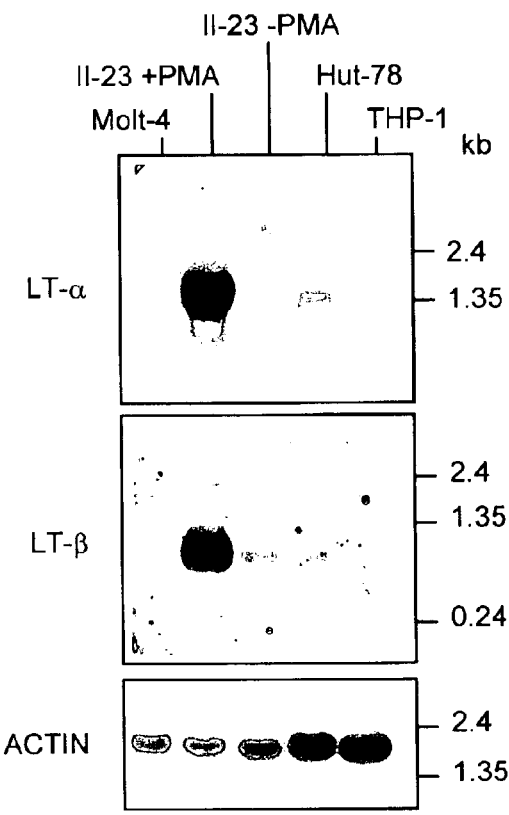
FIG. 15 depicts northern analysis of LT-α and LT-β expression. A) Northern blot of several cell lines showing specific expression of both LT genes in only Hut-78 and II-23.D7 cells. B) Time course of PMA induction of LT-α and LT-β mRNAs in II-23.D7 cells. C) Similar analysis of human peripheral blood lymphocytes activated with either anti-CD3 or IL-2 alone.
Figure 15B:
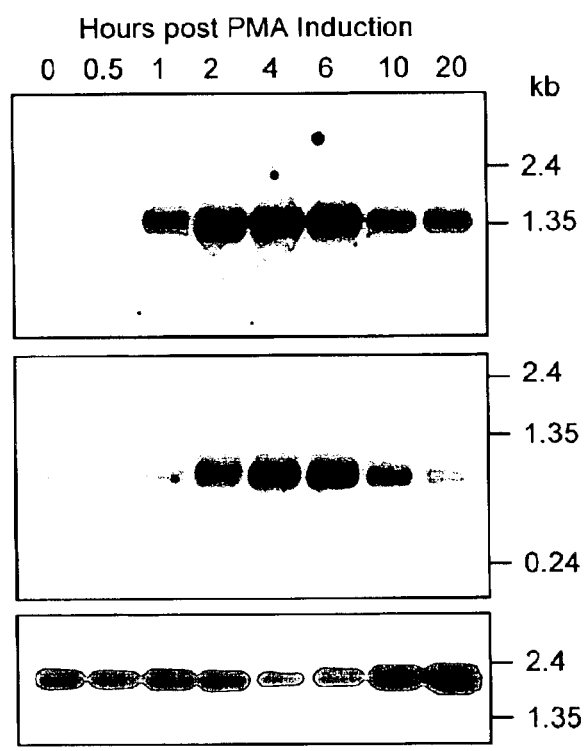
Figure 15C:
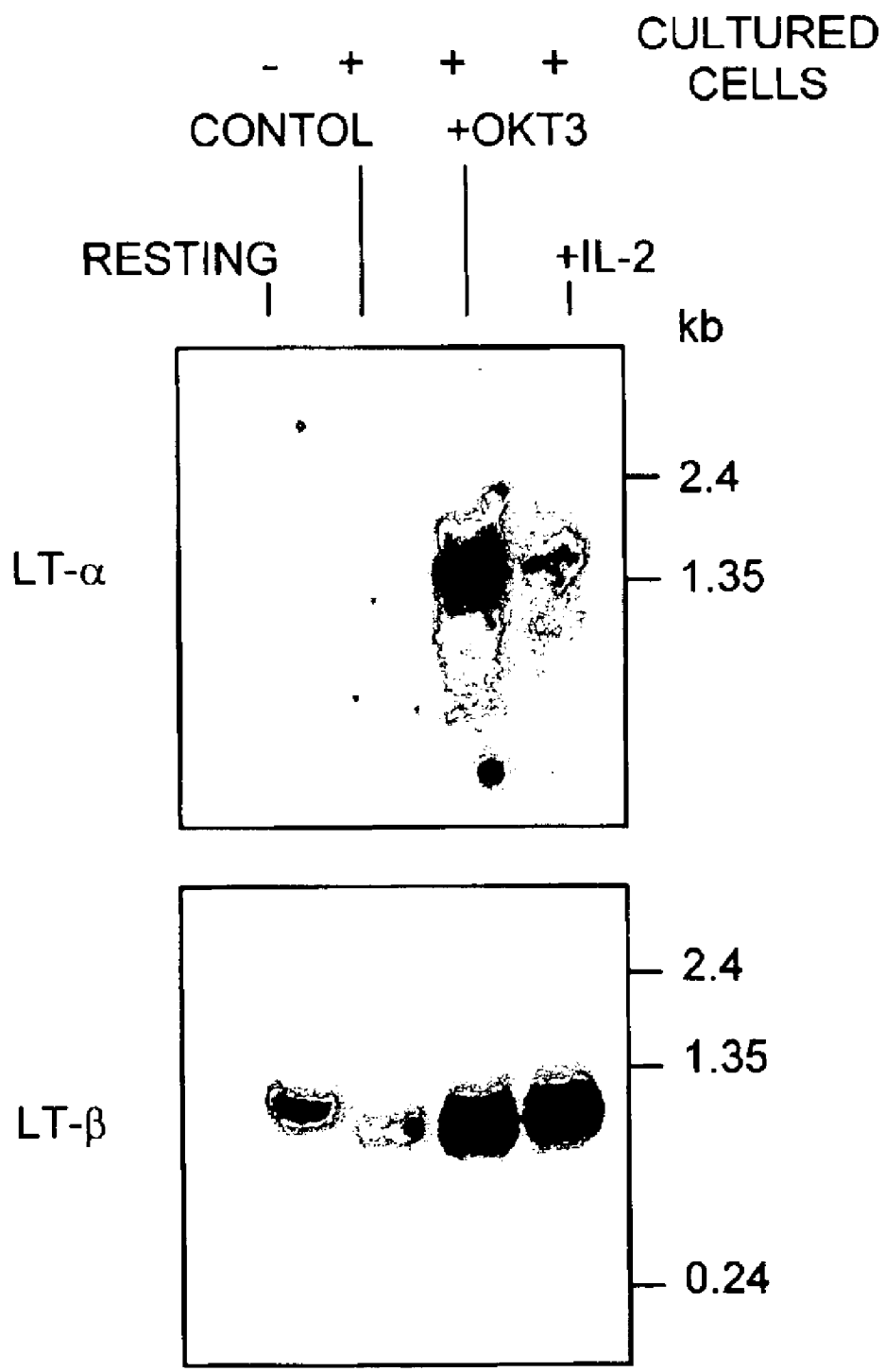

Northern analysis of II-23.D7 cells showed hybridization of the LT-β cDNA to a 0.9–1.0 kb mRNA indicating that the cloned cDNA represents essentially all of the transcribed gene. See FIG. 15. The LT-β gene was expressed at low levels in untreated II-23.D7 hybridoma cells; however, upon cell activation with phorbol ester mRNA levels increased dramatically. See FIG. 16.

Example 11
Homology between LT-β and other Members of the TNF Family of Lymphokines Cloning of the cDNA encoding LT-β revealed that LT-β is a type-II membrane protein with significant homology to TNF, LT-α and the ligand for the CD40 receptor. These proteins are known to bind to members of the TNF/NGF receptor family. LT-β, TNF, LT-α and the ligand for the CD-40 receptor share four regions of sequence conservation in the extracellular domain. See FIG. 13. These domains are located on the face of the TNF and LT-α crystal structures and are likely to be involved in intersubunit interactions.

Example 12
Determination of the 5' End of LT-β Reveals Several Possible Start Sites The 5' mRNA sequence was determined by primer extension analysis. Primer extension analysis revealed that the transcriptional start site for the LT-β protein was approximately 7–9 base pairs upstream of the methionine ATG. Thus, the mRNA possesses at least 3 possible translation start sites, the Met-1, Leu-4 and Leu-6 codons. Transient experiments with clone 12 showed that one or both of the Leu-4 or Leu-6 start sites is functional. The 5' mRNA sequence was verified by determining the LT-β genomic sequence using a cosmid clone 031A, described above, and dideoxynucleic acid sequencing.

---

We claim:

1. A method for treating or lessening the advancement, severity, or effects of neoplasia, comprising administering an effective amount of a composition comprising a pharmaceutically acceptable carrier and a polypeptide complex comprising a first polypeptide selected from a group consisting of
   (a) a polypeptide comprising the amino acid sequence defined by SEQ ID NO: 2;
   (b) a polypeptide comprising the amino acid sequence defined by SEQ ID NO: 4;
   (c) a polypeptide comprising the amino acid sequence defined by SEQ ID NO: 6;
   (d) a polypeptide comprising the amino acid sequence defined by SEQ ID NO: 2 wherein the amino acids Leu Gly Leu at the amino terminus of said sequence are replaced by a single Met or Leu residue; and
   a second polypeptide which is lymphotoxin-α.

2. The method of claim 1, wherein the first polypeptide is a polypeptide comprising the amino acid sequence defined by SEQ ID NO: 2.

3. The method of claim 1, wherein the first polypeptide is a polypeptide comprising the amino acid sequence defined by SEQ ID NO: 4.

4. The method of claim 1, wherein the first polypeptide is a polypeptide comprising the amino acid sequence defined by SEQ ID NO: 6.

5. The method of claim 1, wherein the first polypeptide is a polypeptide comprising the amino acid sequence defined by SEQ ID NO: 2, wherein the amino acids Leu Gly Leu at the aimno terminus of said sequence are replaced by a single Met or Leu residue.

* * * * *